(12) United States Patent
Glenn et al.

(10) Patent No.: US 8,728,793 B2
(45) Date of Patent: May 20, 2014

(54) AMPHIPATHIC ALPHA-HELICAL PEPTIDE COMPOSITIONS AS ANTIVIRAL AGENTS

(75) Inventors: Jeffrey Glenn, Palo Alto, CA (US);
Nam-Joon Cho, Stanford, CA (US);
Curtis W. Frank, Cupertino, CA (US);
Kwang Ho Cheong, Yongin-Si (KR)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/172,796

(22) Filed: Jul. 14, 2008

(65) Prior Publication Data
US 2009/0105151 A1 Apr. 23, 2009

Related U.S. Application Data

(60) Provisional application No. 60/961,457, filed on Jul. 19, 2007, provisional application No. 61/080,210, filed on Jul. 11, 2008.

(51) Int. Cl.
*C12N 7/04* (2006.01)
*C12N 7/08* (2006.01)
*A61K 39/29* (2006.01)

(52) U.S. Cl.
USPC .................. 435/236; 424/228.1; 530/300

(58) Field of Classification Search
None
See application file for complete search history.

(56) References Cited

U.S. PATENT DOCUMENTS

| | | |
|---|---|---|
| 2003/0022829 A1 | 1/2003 | Maury et al. |
| 2004/0265792 A1 | 12/2004 | Glenn et al. |
| 2007/0036825 A1 | 2/2007 | Stapleton et al. |
| 2007/0073039 A1 | 3/2007 | Chisari |

FOREIGN PATENT DOCUMENTS

| | | |
|---|---|---|
| WO | WO02088731 A2 | 11/2002 |
| WO | WO2006110350 A2 | 10/2006 |
| WO | WO2007041487 | 4/2007 |
| WO | WO2008086042 | 7/2008 |
| WO | WO2008133759 | 11/2008 |

OTHER PUBLICATIONS

U.S. Appl. No. 60/879,727, filed Jan. 2007, Chisari, Francis.*
Fields Virology, Third Edition, Fields et al. Eds., Lippincott Williams & Wilkens, Philadelphia, 1996, pp. 1139 and 1354-1355.*
Tellinghuisen et al., "Function follows form: The structure of the N-terminal domain of HCV NS5A," Hepatology, vol. 42 No. 3, pp. 732-735 (Sep. 2005).*
Moradpour et al., "Membrane Association of the RNA-Dependent RNA Polymerase is Essential for Hepatitis C Virus RNA Replication," Journal of Virology, vol. 78 No. 23, pp. 13278-13284 (Dec. 2004).*
Puyal et al., "Design of a short membrane-destabilizing peptide covalently bound to liposomes," Biochimica and Biophysica Acta, vol. 1195 No. 1, pp. 259-266 (Nov. 1994).*
Srinivas et al., "Antiviral effects of apolipoprotein A-I and its synthetic amphipathic peptide analogs," Virology, vol. 176 No. 1, pp. 48-57 (May 1990).*
Brass et al. An amino-terminal Amphipathic the Journal Biol. Chem., vol. 277, Issue 10, 8130-8139, Mar. 8, 2002.
Bellomio, A., Oliveira, R.G., Maggio, B. & Morero, R.D. Penetration and interactions of the antimicrobial peptide, microcin J25, into uncharged phospholipid monolayers. J Colloid Interface Sci 285, 118-124 (2005).
Gao, L., Aizaki, H., He, J.W. & Lai, M.M. Interactions between viral nonstructural proteins and host protein hVAP-33 mediate the formation of hepatitis C virus RNA replication complex on lipid raft. J Virol 78, 3480-3488 (2004).
Gidalevitz, D. et al. Interaction of antimicrobial peptide protegrin with biomembranes. Proc Natl Acad Sci U S A 100, 6302-6307 (2003).
Hengerer, A. et al. Bioactive films. Trends and New Applications of Thin Films 287-2, 169-177 (1998).
Johnson, J.M., Ha, T., Chu, S. & Boxer, S.G. Early steps of supported bilayer formation probed by single vesicle fluorescence assays. Biophys J 83, 3371-3379 (2002).
Kasemo, B. & Lausmaa, J. Biomaterial and implant surfaces: a surface science approach. Int J Oral Maxillofac Implants 3, 247-259 (1988).
Kasemo, B. & Lausmaa, J. Biomaterial and implant surfaces: on the role of cleanliness, contamination, and preparation procedures. J Biomed Mater Res 22, 145-158 (1988).
Kataoka, S. et al. Investigation of water structure at the TiO2/aqueous interface. Langmuir 20, 1662-1666 (2004).
Keller, C. A. et al. Formation of supported membranes from vesicles. Phys Rev Lett 2000, 84, (23), 5443-6.
Keller, C. A.; Kasemo, B., Surface specific kinetics of lipid vesicle adsorption measured with a quartz crystal microbalance. Biophys J 1998, 75, (3), 1397-1402.
Lauer, G.M. & Walker, B.D. Hepatitis C virus infection. N. Engl J Med 345, 41-52 (2001).
Mecke, A., al. et al Membrane thinning due to antimicrobial peptide binding: an atomic force microscopy study of MSI-78 in lipid bilayers. Biophys J 89, 4043-4050 (2005).
Penin, F. et al. Structure and function of the membrane anchor domain of hepatitis C virus nonstructural protein 5A. J Biol Chem (2004) 24;279(39):40835-43.
Plant, A.L. Supported Hybrid Bilayer Membranes as Rugged Cell Membrane Mimics. Langmuir 15, 5128-5135 (1999).

(Continued)

*Primary Examiner* — Stacy B. Chen
(74) *Attorney, Agent, or Firm* — Paula A. Borden; Bozicevic, Field & Francis LLP.

(57) ABSTRACT

The invention features methods and compositions that exploit the ability of amphipathic alpha-helical (AH) peptides to cause disruption of lipid-containing vesicles, such as enveloped viruses, in a size-dependent manner.

29 Claims, 14 Drawing Sheets

(56) References Cited

OTHER PUBLICATIONS

Power, M. et al. Aerogels as Biosensors: Viral Particle Detection by Bacteria Immobilized on Large Pore Aerogel. Journal of Non-Crystalline Solids 285, 303-308 (2001).

Reimhult, E., Hook, F. & Kasemo, B. Intact vesicle adsorption and supported biomembrane formation from vesicles in solution: Influence of surface chemistry, vesicle size, temperature, and osmotic pressure. Langmuir 19, 1681-1691 (2003).

Reimhult, E.; Hook, F.; Kasemo, B. Temperature dependence of formation of a supported phospholipid bilayer from vesicles on SiO2. Phys Rev E Stat Nonlin Soft Matter Phys 2002, 66, (5 Pt 1), 051905.

Reimhult, E.; Hook, F.; Kasemo, B. Vesicle adsorption on SiO2 and TiO2: Dependence on vesicle size. Journal of Chemical Physics 2002, 117, (16), 7401-7404.

Sackmann, E. Supported Membranes: Scientific and Practical Applications. Science 271, 43-48 (1996).

Sato, H. & Feix, J.B. Peptide-membrane interactions and mechanisms of membrane destruction by amphipathic alpha-helical antimicrobial peptides. Biochim Biophys Acta (2006).

Sinner, E.K. & Knoll, W. Functional tethered membranes. Curr Opin Chem Biol 5, 705-711 (2001).

Voinova, M.V., Jonson, M. & Kasemo, B. 'Missing mass' effect in biosensor's QCM applications. Biosensors & Bioelectronics 17, 835-841 (2002).

Cho et al. Employing an amphipathic viral peptide to create a lipid bilayer on Au and TiO2. J. Am. Chem. Soc.,2007, vol. 129, pp. 10050-10051.

Cho et al. Binding dynamics of hepatitis C virus' NS5A amphipathic peptide to cell and model membranes. Journal of Virology, 2007, vol. 81, No. 12, pp. 6682-6689.

Cheng et al. A virocidal amphipathic a-helical peptide that inhibits hepatitis C virus infection in vitro. PNAS, 2008, vol. 105, No. 8, pp. 3088-3093.

Cho et al. Employing two different quartz crystal microbalance models to study changes in visciekelastic behavior upon transformation of lipid vesicles to a bilayer on a gold surface. Anal. Chem. 2007, 79, 7027-7035.

Lamaziere et al. Non-metabolic membrane tubulation and permeability induced by bioactive peptides. PLoS ONE, 2007, issue 2, e201, pp. 1-11.

Bighian, et al. An amphipathic alpha-helical synthetic peptide analogue of melittin inhibits herpes simplex virus-1 (HSV-1)-induced cell fusion and virus spread. Peptides. 1997;18(2):177-83.

Eisenberg and Wesson. The most highly amphiphilic alpha-helices include two amino acid segments in human immunodeficiency virus glycoprotein 41. Biopolymers. Jan. 1990:29(1):171-7.

Elazar, et al. Amphipathic helix-dependent localization of NS5A mediates hepatitis C virus RNA replication. J Virol. May 2003;77(10):6055-61.

Cho, et al. Mechanism of an amphipathic alpha-helical peptide's antiviral activity involves size-dependent virus particle lysis. ACS Chem Biol. Dec. 18, 2009;4(12):1061-7.

* cited by examiner

SEQUENCE LISTING

```
<160> NUMBER OF SEQ ID NOS: 91

<210> SEQ ID NO 1
<211> LENGTH: 14
<212> TYPE: PRT
<213> ORGANISM: Hepatitis C virus
<220> FEATURE:
<221> NAME/KEY: VARIANT
<222> LOCATION: 4
<223> OTHER INFORMATION: X is charged or polar residue, such as R, H, W,
      or Y, especially a positively charged residue such as
      R, K or H
<220> FEATURE:
<221> NAME/KEY: VARIANT
<222> LOCATION: 5
<223> OTHER INFORMATION: X is any amino acid residue, and can be a
      residue other than an positively charged residue, e.g., D,
      I, or T, particularly negatively charged residue
      such as D or E
<220> FEATURE:
<221> NAME/KEY: VARIANT
<222> LOCATION: 6
<223> OTHER INFORMATION: X is other than a charged residue, and can be a
      nonpolar (hydrophobic) residue, such as V or I
<220> FEATURE:
<221> NAME/KEY: VARIANT
<222> LOCATION: 7
<223> OTHER INFORMATION: X is a nonpolar (hydrophobic) residue, such as
      W or V
<220> FEATURE:
```

```
<221> NAME/KEY: VARIANT
<222> LOCATION: 8
<223> OTHER INFORMATION: X is a charged (e.g., negatively charged) or
      polar, uncharged residue, such as D, E, or N,
      particularly a negatively charged residue such as
      D or E
<220> FEATURE:
<221> NAME/KEY: VARIANT
<222> LOCATION: 10
<223> OTHER INFORMATION: X is other than a charged residue, and can be a
      nonpolar (hydrophobic) residue such as I or V
<220> FEATURE:
<221> NAME/KEY: VARIANT
<222> LOCATION: 11
<223> OTHER INFORMATION: X is polar, uncharged residue, nonpolar
      (hydrophobic) residue, or negatively charged
      residue, such as C or L or E, particularly a
      polar, uncharged residue, nonpolar (hydrophobic)
      residue, such as C or L
<220> FEATURE:
<221> NAME/KEY: VARIANT
<222> LOCATION: 12
<223> OTHER INFORMATION: X is a polar, uncharged residue, a nonpolar
      (hydrophobic) residue, or a positively charged
      residue, such as T, S, I , or H, particularly a
      polar, uncharged residue such as T
<220> FEATURE:
<221> NAME/KEY: VARIANT
<222> LOCATION: 13
<223> OTHER INFORMATION: X is a nonpolar (hydrophobic) residue, such as
      V, I or W
<220> FEATURE:
<221> NAME/KEY: VARIANT
<222> LOCATION: 14
<223> OTHER INFORMATION: X is C or L

<400> SEQUENCE: 1

Ser Trp Leu Xaa Xaa Xaa Xaa Xaa Trp Xaa Xaa Xaa Xaa Xaa
1               5                   10

<210> SEQ ID NO 2
<211> LENGTH: 14
<212> TYPE: PRT
<213> ORGANISM: Hepatitis C virus

<400> SEQUENCE: 2

Ser Trp Leu Arg Asp Val Trp Asp Trp Ile Cys Thr Val Leu
1               5                   10

<210> SEQ ID NO 3
<211> LENGTH: 14
<212> TYPE: PRT
<213> ORGANISM: Hepatitis C virus

<400> SEQUENCE: 3

Ser Trp Leu Arg Asp Val Trp Asp Trp Val Cys Thr Ile Leu
1               5                   10

<210> SEQ ID NO 4
<211> LENGTH: 14
<212> TYPE: PRT
<213> ORGANISM: Hepatitis C virus

<400> SEQUENCE: 4

Ser Trp Leu Arg Asp Ile Trp Glu Trp Val Leu Ser Ile Leu
1               5                   10

<210> SEQ ID NO 5
<211> LENGTH: 14
<212> TYPE: PRT
<213> ORGANISM: Hepatitis C virus
```

```
<400> SEQUENCE: 5

Ser Trp Leu Arg Ile Ile Trp Asp Trp Val Cys Ser Trp Cys
1               5                   10

<210> SEQ ID NO 6
<211> LENGTH: 14
<212> TYPE: PRT
<213> ORGANISM: Hepatitis C virus

<400> SEQUENCE: 6

Ser Trp Leu Arg Thr Ile Trp Asp Trp Val Cys Ser Val Cys
1               5                   10

<210> SEQ ID NO 7
<211> LENGTH: 14
<212> TYPE: PRT
<213> ORGANISM: Hepatitis C virus

<400> SEQUENCE: 7

Ser Trp Leu His Asp Ile Trp Asp Trp Val Cys Ile Val Cys
1               5                   10

<210> SEQ ID NO 8
<211> LENGTH: 14
<212> TYPE: PRT
<213> ORGANISM: Hepatitis C virus

<400> SEQUENCE: 8

Ser Trp Leu Trp Asp Val Trp Asp Trp Val Leu His Val Leu
1               5                   10

<210> SEQ ID NO 9
<211> LENGTH: 14
<212> TYPE: PRT
<213> ORGANISM: Hepatitis C virus

<400> SEQUENCE: 9

Ser Trp Leu Tyr Asp Ile Val Asn Trp Val Cys Thr Val Cys
1               5                   10

<210> SEQ ID NO 10
<211> LENGTH: 14
<212> TYPE: PRT
<213> ORGANISM: Hepatitis C virus

<400> SEQUENCE: 10

Ser Trp Leu Arg Asp Ile Trp Asp Trp Val Cys Thr Val Cys
1               5                   10

<210> SEQ ID NO 11
<211> LENGTH: 14
<212> TYPE: PRT
<213> ORGANISM: Hepatitis C virus

<400> SEQUENCE: 11

Ser Trp Leu Arg Asp Ile Trp Asp Trp Ile Cys Glu Val Leu
1               5                   10

<210> SEQ ID NO 12
<211> LENGTH: 21
<212> TYPE: PRT
<213> ORGANISM: Hepatitis C virus

<400> SEQUENCE: 12

Leu Arg Asp Ile Trp Asp Trp Ile Cys Glu Val Leu Ser Asp Phe Lys
```

```
                1               5                   10                  15

Thr Trp Leu Lys Ala
            20

<210> SEQ ID NO 13
<211> LENGTH: 24
<212> TYPE: PRT
<213> ORGANISM: Hepatitis C virus

<400> SEQUENCE: 13

Trp Leu Arg Asp Val Trp Asp Trp Ile Cys Thr Val Leu Thr Asp Phe
1               5                   10                  15

Lys Thr Trp Leu Gln Ser Lys Leu
            20

<210> SEQ ID NO 14
<211> LENGTH: 24
<212> TYPE: PRT
<213> ORGANISM: Hepatitis C virus

<400> SEQUENCE: 14

Trp Leu Arg Asp Val Trp Asp Trp Val Cys Thr Ile Leu Thr Asp Phe
1               5                   10                  15

Lys Asn Trp Leu Thr Ser Lys Leu
            20

<210> SEQ ID NO 15
<211> LENGTH: 24
<212> TYPE: PRT
<213> ORGANISM: Hepatitis C virus

<400> SEQUENCE: 15

Trp Leu Arg Asp Ile Trp Glu Trp Val Leu Ser Ile Leu Thr Asp Phe
1               5                   10                  15

Lys Asn Trp Leu Ser Ala Lys Leu
            20

<210> SEQ ID NO 16
<211> LENGTH: 24
<212> TYPE: PRT
<213> ORGANISM: Hepatitis C virus

<400> SEQUENCE: 16

Trp Leu Arg Ile Ile Trp Asp Trp Val Cys Ser Val Val Ser Asp Phe
1               5                   10                  15

Lys Thr Trp Leu Ser Ala Lys Ile
            20

<210> SEQ ID NO 17
<211> LENGTH: 24
<212> TYPE: PRT
<213> ORGANISM: Hepatitis C virus

<400> SEQUENCE: 17

Trp Leu Arg Thr Ile Trp Asp Trp Val Cys Ser Val Leu Ala Asp Phe
1               5                   10                  15

Lys Ala Trp Leu Ser Ala Lys Ile
            20

<210> SEQ ID NO 18
<211> LENGTH: 24
<212> TYPE: PRT
<213> ORGANISM: Hepatitis C virus
```

```
<400> SEQUENCE: 18

Trp Leu His Asp Ile Trp Asp Trp Val Cys Ile Val Leu Ser Asp Phe
1               5                   10                  15

Lys Thr Trp Leu Ser Ala Lys Ile
            20

<210> SEQ ID NO 19
<211> LENGTH: 24
<212> TYPE: PRT
<213> ORGANISM: Hepatitis C virus

<400> SEQUENCE: 19

Trp Leu Trp Asp Val Trp Asp Trp Val Leu His Val Leu Ser Asp Phe
1               5                   10                  15

Lys Thr Cys Leu Lys Ala Lys Phe
            20

<210> SEQ ID NO 20
<211> LENGTH: 24
<212> TYPE: PRT
<213> ORGANISM: Hepatitis C virus

<400> SEQUENCE: 20

Trp Leu Tyr Asp Ile Val Asn Trp Val Cys Thr Val Leu Ala Asp Phe
1               5                   10                  15

Lys Leu Trp Leu Gly Ala Lys Ile
            20

<210> SEQ ID NO 21
<211> LENGTH: 24
<212> TYPE: PRT
<213> ORGANISM: Hepatitis C virus

<400> SEQUENCE: 21

Trp Leu Arg Asp Ile Trp Asp Trp Val Cys Thr Val Leu Ser Asp Phe
1               5                   10                  15

Arg Val Trp Leu Lys Ser Lys Leu
            20

<210> SEQ ID NO 22
<211> LENGTH: 25
<212> TYPE: PRT
<213> ORGANISM: Hepatitis C virus

<400> SEQUENCE: 22

Ser Trp Leu Arg Asp Val Trp Asp Trp Ile Cys Thr Val Leu Thr Asp
1               5                   10                  15

Phe Lys Thr Trp Leu Gln Ser Lys Leu
            20                  25

<210> SEQ ID NO 23
<211> LENGTH: 25
<212> TYPE: PRT
<213> ORGANISM: Hepatitis C virus

<400> SEQUENCE: 23

Ser Trp Leu Arg Asp Val Trp Asp Trp Val Cys Thr Ile Leu Thr Asp
1               5                   10                  15

Phe Lys Asn Trp Leu Thr Ser Lys Leu
            20                  25
```

-continued

```
<210> SEQ ID NO 24
<211> LENGTH: 25
<212> TYPE: PRT
<213> ORGANISM: Hepatitis C virus

<400> SEQUENCE: 24

Ser Trp Leu Arg Asp Ile Trp Glu Trp Val Leu Ser Ile Leu Thr Asp
1               5                   10                  15

Phe Lys Asn Trp Leu Ser Ala Lys Leu
            20                  25

<210> SEQ ID NO 25
<211> LENGTH: 24
<212> TYPE: PRT
<213> ORGANISM: Hepatitis C virus

<400> SEQUENCE: 25

Ser Trp Leu Arg Ile Ile Trp Asp Trp Val Cys Ser Trp Ser Asp Phe
1               5                   10                  15

Lys Thr Trp Leu Ser Ala Lys Ile
            20

<210> SEQ ID NO 26
<211> LENGTH: 25
<212> TYPE: PRT
<213> ORGANISM: Hepatitis C virus

<400> SEQUENCE: 26

Ser Trp Leu Arg Thr Ile Trp Asp Trp Val Cys Ser Val Leu Ala Asp
1               5                   10                  15

Phe Lys Ala Trp Leu Ser Ala Lys Ile
            20                  25

<210> SEQ ID NO 27
<211> LENGTH: 25
<212> TYPE: PRT
<213> ORGANISM: Hepatitis C virus

<400> SEQUENCE: 27

Ser Trp Leu His Asp Ile Trp Asp Trp Val Cys Ile Val Leu Ser Asp
1               5                   10                  15

Phe Lys Thr Trp Leu Ser Ala Lys Ile
            20                  25

<210> SEQ ID NO 28
<211> LENGTH: 25
<212> TYPE: PRT
<213> ORGANISM: Hepatitis C virus

<400> SEQUENCE: 28

Ser Trp Leu Trp Asp Val Trp Asp Trp Val Leu His Val Leu Ser Asp
1               5                   10                  15

Phe Lys Thr Cys Leu Lys Ala Lys Phe
            20                  25

<210> SEQ ID NO 29
<211> LENGTH: 25
<212> TYPE: PRT
<213> ORGANISM: Hepatitis C virus

<400> SEQUENCE: 29

Ser Trp Leu Tyr Asp Ile Val Asn Trp Val Cys Thr Val Leu Ala Asp
1               5                   10                  15
```

Phe Lys Leu Trp Leu Gly Ala Lys Ile
            20                  25

<210> SEQ ID NO 30
<211> LENGTH: 25
<212> TYPE: PRT
<213> ORGANISM: Hepatitis C virus

<400> SEQUENCE: 30

Ser Trp Leu Arg Asp Ile Trp Asp Trp Val Cys Thr Val Leu Ser Asp
1               5                   10                  15

Phe Arg Val Trp Leu Lys Ser Lys Leu
            20                  25

<210> SEQ ID NO 31
<211> LENGTH: 24
<212> TYPE: PRT
<213> ORGANISM: Hepatitis C virus

<400> SEQUENCE: 31

Ser Gly Ser Leu Arg Asp Ile Trp Asp Trp Ile Cys Glu Val Leu Ser
1               5                   10                  15

Asp Phe Lys Thr Trp Leu Lys Ala
            20

<210> SEQ ID NO 32
<211> LENGTH: 27
<212> TYPE: PRT
<213> ORGANISM: Hepatitis C virus

<400> SEQUENCE: 32

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu
            20                  25

<210> SEQ ID NO 33
<211> LENGTH: 27
<212> TYPE: PRT
<213> ORGANISM: Hepatitis C virus

<400> SEQUENCE: 33

Ser Gly Ser Trp Leu Arg Asp Val Trp Asp Trp Val Cys Thr Ile Leu
1               5                   10                  15

Thr Asp Phe Lys Asn Trp Leu Thr Ser Lys Leu
            20                  25

<210> SEQ ID NO 34
<211> LENGTH: 27
<212> TYPE: PRT
<213> ORGANISM: Hepatitis C virus

<400> SEQUENCE: 34

Ser Gly Ser Trp Leu Arg Asp Ile Trp Glu Trp Val Leu Ser Ile Leu
1               5                   10                  15

Thr Asp Phe Lys Asn Trp Leu Ser Ala Lys Leu
            20                  25

<210> SEQ ID NO 35
<211> LENGTH: 26
<212> TYPE: PRT
<213> ORGANISM: Hepatitis C virus

<400> SEQUENCE: 35

```
Ser Gly Ser Trp Leu Arg Ile Ile Trp Asp Trp Val Cys Ser Trp Ser
1               5                   10                  15

Asp Phe Lys Thr Trp Leu Ser Ala Lys Ile
            20                  25

<210> SEQ ID NO 36
<211> LENGTH: 27
<212> TYPE: PRT
<213> ORGANISM: Hepatitis C virus

<400> SEQUENCE: 36

Ser Gly Ser Trp Leu Arg Thr Ile Trp Asp Trp Val Cys Ser Val Leu
1               5                   10                  15

Ala Asp Phe Lys Ala Trp Leu Ser Ala Lys Ile
            20                  25

<210> SEQ ID NO 37
<211> LENGTH: 27
<212> TYPE: PRT
<213> ORGANISM: Hepatitis C virus

<400> SEQUENCE: 37

Ser Gly Ser Trp Leu His Asp Ile Trp Asp Trp Val Cys Ile Val Leu
1               5                   10                  15

Ser Asp Phe Lys Thr Trp Leu Ser Ala Lys Ile
            20                  25

<210> SEQ ID NO 38
<211> LENGTH: 27
<212> TYPE: PRT
<213> ORGANISM: Hepatitis C virus

<400> SEQUENCE: 38

Ser Gly Ser Trp Leu Trp Asp Val Trp Asp Trp Val Leu His Val Leu
1               5                   10                  15

Ser Asp Phe Lys Thr Cys Leu Lys Ala Lys Phe
            20                  25

<210> SEQ ID NO 39
<211> LENGTH: 27
<212> TYPE: PRT
<213> ORGANISM: Hepatitis C virus

<400> SEQUENCE: 39

Ser Gly Ser Trp Leu Tyr Asp Ile Val Asn Trp Val Cys Thr Val Leu
1               5                   10                  15

Ala Asp Phe Lys Leu Trp Leu Gly Ala Lys Ile
            20                  25

<210> SEQ ID NO 40
<211> LENGTH: 27
<212> TYPE: PRT
<213> ORGANISM: Hepatitis C virus

<400> SEQUENCE: 40

Ser Gly Ser Trp Leu Arg Asp Ile Trp Asp Trp Val Cys Thr Val Leu
1               5                   10                  15

Ser Asp Phe Arg Val Trp Leu Lys Ser Lys Leu
            20                  25

<210> SEQ ID NO 41
<211> LENGTH: 26
```

```
<212> TYPE: PRT
<213> ORGANISM: Hepatitis C virus

<400> SEQUENCE: 41

Gly Ser Trp Leu Arg Asp Val Trp Asp Trp Ile Cys Thr Val Leu Thr
1               5                   10                  15

Asp Phe Lys Thr Trp Leu Gln Ser Lys Leu
            20                  25

<210> SEQ ID NO 42
<211> LENGTH: 26
<212> TYPE: PRT
<213> ORGANISM: Hepatitis C virus

<400> SEQUENCE: 42

Gly Ser Trp Leu Arg Asp Val Trp Asp Trp Val Cys Thr Ile Leu Thr
1               5                   10                  15

Asp Phe Lys Asn Trp Leu Thr Ser Lys Leu
            20                  25

<210> SEQ ID NO 43
<211> LENGTH: 26
<212> TYPE: PRT
<213> ORGANISM: Hepatitis C virus

<400> SEQUENCE: 43

Gly Ser Trp Leu Arg Asp Ile Trp Glu Trp Val Leu Ser Ile Leu Thr
1               5                   10                  15

Asp Phe Lys Asn Trp Leu Ser Ala Lys Leu
            20                  25

<210> SEQ ID NO 44
<211> LENGTH: 25
<212> TYPE: PRT
<213> ORGANISM: Hepatitis C virus

<400> SEQUENCE: 44

Gly Ser Trp Leu Arg Ile Ile Trp Asp Trp Val Cys Ser Trp Ser Asp
1               5                   10                  15

Phe Lys Thr Trp Leu Ser Ala Lys Ile
            20                  25

<210> SEQ ID NO 45
<211> LENGTH: 26
<212> TYPE: PRT
<213> ORGANISM: Hepatitis C virus

<400> SEQUENCE: 45

Gly Ser Trp Leu Arg Thr Ile Trp Asp Trp Val Cys Ser Val Leu Ala
1               5                   10                  15

Asp Phe Lys Ala Trp Leu Ser Ala Lys Ile
            20                  25

<210> SEQ ID NO 46
<211> LENGTH: 26
<212> TYPE: PRT
<213> ORGANISM: Hepatitis C virus

<400> SEQUENCE: 46

Gly Ser Trp Leu His Asp Ile Trp Asp Trp Val Cys Ile Val Leu Ser
1               5                   10                  15

Asp Phe Lys Thr Trp Leu Ser Ala Lys Ile
            20                  25
```

```
<210> SEQ ID NO 47
<211> LENGTH: 26
<212> TYPE: PRT
<213> ORGANISM: Hepatitis C virus

<400> SEQUENCE: 47

Gly Ser Trp Leu Trp Asp Val Trp Asp Trp Val Leu His Val Leu Ser
1               5                   10                  15

Asp Phe Lys Thr Cys Leu Lys Ala Lys Phe
            20                  25

<210> SEQ ID NO 48
<211> LENGTH: 26
<212> TYPE: PRT
<213> ORGANISM: Hepatitis C virus

<400> SEQUENCE: 48

Gly Ser Trp Leu Tyr Asp Ile Val Asn Trp Val Cys Thr Val Leu Ala
1               5                   10                  15

Asp Phe Lys Leu Trp Leu Gly Ala Lys Ile
            20                  25

<210> SEQ ID NO 49
<211> LENGTH: 26
<212> TYPE: PRT
<213> ORGANISM: Hepatitis C virus

<400> SEQUENCE: 49

Gly Ser Trp Leu Arg Asp Ile Trp Asp Trp Val Cys Thr Val Leu Ser
1               5                   10                  15

Asp Phe Arg Val Trp Leu Lys Ser Lys Leu
            20                  25

<210> SEQ ID NO 50
<211> LENGTH: 15
<212> TYPE: PRT
<213> ORGANISM: Hepatitis C virus

<400> SEQUENCE: 50

Ser Trp Leu Arg Asp Val Trp Asp Trp Ile Cys Thr Val Leu Thr
1               5                   10                  15

<210> SEQ ID NO 51
<211> LENGTH: 15
<212> TYPE: PRT
<213> ORGANISM: Hepatitis C virus

<400> SEQUENCE: 51

Ser Trp Leu Arg Asp Val Trp Asp Trp Val Cys Thr Ile Leu Thr
1               5                   10                  15

<210> SEQ ID NO 52
<211> LENGTH: 15
<212> TYPE: PRT
<213> ORGANISM: Hepatitis C virus

<400> SEQUENCE: 52

Ser Trp Leu Arg Asp Ile Trp Glu Trp Val Leu Ser Ile Leu Thr
1               5                   10                  15

<210> SEQ ID NO 53
<211> LENGTH: 15
<212> TYPE: PRT
```

<213> ORGANISM: Hepatitis C virus

<400> SEQUENCE: 53

Ser Trp Leu Arg Ile Ile Trp Asp Trp Val Cys Ser Trp Ser Asp
1               5                   10                  15

<210> SEQ ID NO 54
<211> LENGTH: 15
<212> TYPE: PRT
<213> ORGANISM: Hepatitis C virus

<400> SEQUENCE: 54

Ser Trp Leu Arg Thr Ile Trp Asp Trp Val Cys Ser Val Leu Ala
1               5                   10                  15

<210> SEQ ID NO 55
<211> LENGTH: 15
<212> TYPE: PRT
<213> ORGANISM: Hepatitis C virus

<400> SEQUENCE: 55

Ser Trp Leu His Asp Ile Trp Asp Trp Val Cys Ile Val Leu Ser
1               5                   10                  15

<210> SEQ ID NO 56
<211> LENGTH: 15
<212> TYPE: PRT
<213> ORGANISM: Hepatitis C virus

<400> SEQUENCE: 56

Ser Trp Leu Trp Asp Val Trp Asp Trp Val Leu His Val Leu Ser
1               5                   10                  15

<210> SEQ ID NO 57
<211> LENGTH: 15
<212> TYPE: PRT
<213> ORGANISM: Hepatitis C virus

<400> SEQUENCE: 57

Ser Trp Leu Tyr Asp Ile Val Asn Trp Val Cys Thr Val Leu Ala
1               5                   10                  15

<210> SEQ ID NO 58
<211> LENGTH: 15
<212> TYPE: PRT
<213> ORGANISM: Hepatitis C virus

<400> SEQUENCE: 58

Ser Trp Leu Arg Asp Ile Trp Asp Trp Val Cys Thr Val Leu Ser
1               5                   10                  15

<210> SEQ ID NO 59
<211> LENGTH: 16
<212> TYPE: PRT
<213> ORGANISM: Hepatitis C virus

<400> SEQUENCE: 59

Ser Trp Leu Arg Asp Val Trp Asp Trp Ile Cys Thr Val Leu Thr Asp
1               5                   10                  15

<210> SEQ ID NO 60
<211> LENGTH: 16
<212> TYPE: PRT
<213> ORGANISM: Hepatitis C virus

<400> SEQUENCE: 60

Ser Trp Leu Arg Asp Val Trp Asp Trp Val Cys Thr Ile Leu Thr Asp
1               5                   10                  15

<210> SEQ ID NO 61
<211> LENGTH: 16
<212> TYPE: PRT
<213> ORGANISM: Hepatitis C virus

<400> SEQUENCE: 61

Ser Trp Leu Arg Asp Ile Trp Glu Trp Val Leu Ser Ile Leu Thr Asp
1               5                   10                  15

<210> SEQ ID NO 62
<211> LENGTH: 16
<212> TYPE: PRT
<213> ORGANISM: Hepatitis C virus

<400> SEQUENCE: 62

Ser Trp Leu Arg Ile Ile Trp Asp Trp Val Cys Ser Trp Ser Asp Phe
1               5                   10                  15

<210> SEQ ID NO 63
<211> LENGTH: 16
<212> TYPE: PRT
<213> ORGANISM: Hepatitis C virus

<400> SEQUENCE: 63

Ser Trp Leu Arg Thr Ile Trp Asp Trp Val Cys Ser Val Leu Ala Asp
1               5                   10                  15

<210> SEQ ID NO 64
<211> LENGTH: 16
<212> TYPE: PRT
<213> ORGANISM: Hepatitis C virus

<400> SEQUENCE: 64

Ser Trp Leu His Asp Ile Trp Asp Trp Val Cys Ile Val Leu Ser Asp
1               5                   10                  15

<210> SEQ ID NO 65
<211> LENGTH: 16
<212> TYPE: PRT
<213> ORGANISM: Hepatitis C virus

<400> SEQUENCE: 65

Ser Trp Leu Trp Asp Val Trp Asp Trp Val Leu His Val Leu Ser Asp
1               5                   10                  15

<210> SEQ ID NO 66
<211> LENGTH: 16
<212> TYPE: PRT
<213> ORGANISM: Hepatitis C virus

<400> SEQUENCE: 66

Ser Trp Leu Tyr Asp Ile Val Asn Trp Val Cys Thr Val Leu Ala Asp
1               5                   10                  15

<210> SEQ ID NO 67
<211> LENGTH: 16
<212> TYPE: PRT
<213> ORGANISM: Hepatitis C virus

<400> SEQUENCE: 67

Ser Trp Leu Arg Asp Ile Trp Asp Trp Val Cys Thr Val Leu Ser Asp
1               5                   10                  15

```
<210> SEQ ID NO 68
<211> LENGTH: 17
<212> TYPE: PRT
<213> ORGANISM: Hepatitis C virus

<400> SEQUENCE: 68

Ser Trp Leu Arg Asp Val Trp Asp Trp Ile Cys Thr Val Leu Thr Asp
1               5                   10                  15

Phe

<210> SEQ ID NO 69
<211> LENGTH: 17
<212> TYPE: PRT
<213> ORGANISM: Hepatitis C virus

<400> SEQUENCE: 69

Ser Trp Leu Arg Asp Val Trp Asp Trp Val Cys Thr Ile Leu Thr Asp
1               5                   10                  15

Phe

<210> SEQ ID NO 70
<211> LENGTH: 17
<212> TYPE: PRT
<213> ORGANISM: Hepatitis C virus

<400> SEQUENCE: 70

Ser Trp Leu Arg Asp Ile Trp Glu Trp Val Leu Ser Ile Leu Thr Asp
1               5                   10                  15

Phe

<210> SEQ ID NO 71
<211> LENGTH: 17
<212> TYPE: PRT
<213> ORGANISM: Hepatitis C virus

<400> SEQUENCE: 71

Ser Trp Leu Arg Ile Ile Trp Asp Trp Val Cys Ser Trp Ser Asp Phe
1               5                   10                  15

Lys

<210> SEQ ID NO 72
<211> LENGTH: 17
<212> TYPE: PRT
<213> ORGANISM: Hepatitis C virus

<400> SEQUENCE: 72

Ser Trp Leu Arg Thr Ile Trp Asp Trp Val Cys Ser Val Leu Ala Asp
1               5                   10                  15

Phe

<210> SEQ ID NO 73
<211> LENGTH: 17
<212> TYPE: PRT
<213> ORGANISM: Hepatitis C virus

<400> SEQUENCE: 73

Ser Trp Leu His Asp Ile Trp Asp Trp Val Cys Ile Val Leu Ser Asp
1               5                   10                  15

Phe
```

-continued

```
<210> SEQ ID NO 74
<211> LENGTH: 17
<212> TYPE: PRT
<213> ORGANISM: Hepatitis C virus

<400> SEQUENCE: 74

Ser Trp Leu Trp Asp Val Trp Asp Trp Val Leu His Val Leu Ser Asp
 1               5                  10                  15
Phe

<210> SEQ ID NO 75
<211> LENGTH: 17
<212> TYPE: PRT
<213> ORGANISM: Hepatitis C virus

<400> SEQUENCE: 75

Ser Trp Leu Tyr Asp Ile Val Asn Trp Val Cys Thr Val Leu Ala Asp
 1               5                  10                  15
Phe

<210> SEQ ID NO 76
<211> LENGTH: 17
<212> TYPE: PRT
<213> ORGANISM: Hepatitis C virus

<400> SEQUENCE: 76

Ser Trp Leu Arg Asp Ile Trp Asp Trp Val Cys Thr Val Leu Ser Asp
 1               5                  10                  15
Phe

<210> SEQ ID NO 77
<211> LENGTH: 30
<212> TYPE: PRT
<213> ORGANISM: Hepatitis C virus

<400> SEQUENCE: 77

Ser Gly Ser Trp Leu Arg Asp Val Trp Asp Trp Ile Cys Thr Val Leu
 1               5                  10                  15
Thr Asp Phe Lys Thr Trp Leu Gln Ser Lys Leu Asp Tyr Lys
                20                  25                  30

<210> SEQ ID NO 78
<211> LENGTH: 27
<212> TYPE: PRT
<213> ORGANISM: Hepatitis C virus
<220> FEATURE:
<221> NAME/KEY: VARIANT
<222> LOCATION: 4, 9, 11, 22
<223> OTHER INFORMATION: X is A or F
<220> FEATURE:
<221> NAME/KEY: VARIANT
<222> LOCATION: 5, 16, 23
<223> OTHER INFORMATION: X is A or K
<220> FEATURE:
<221> NAME/KEY: VARIANT
<222> LOCATION: 6
<223> OTHER INFORMATION: X is A or N
<220> FEATURE:
<221> NAME/KEY: VARIANT
<222> LOCATION: 7, 10, 13, 18
<223> OTHER INFORMATION: X is A or S
<220> FEATURE:
<221> NAME/KEY: VARIANT
<222> LOCATION: 8
<223> OTHER INFORMATION: X is D, I or S
<220> FEATURE:
<221> NAME/KEY: VARIANT
<222> LOCATION: 12
```

```
<223> OTHER INFORMATION: X is E or L
<220> FEATURE:
<221> NAME/KEY: VARIANT
<222> LOCATION: 14
<223> OTHER INFORMATION: X A, E, or W
<220> FEATURE:
<221> NAME/KEY: VARIANT
<222> LOCATION: 15
<223> OTHER INFORMATION: X is D or S
<220> FEATURE:
<221> NAME/KEY: VARIANT
<222> LOCATION: 17
<223> OTHER INFORMATION: X is A, S, or W
<220> FEATURE:
<221> NAME/KEY: VARIANT
<222> LOCATION: 19
<223> OTHER INFORMATION: X is D or L
<220> FEATURE:
<221> NAME/KEY: VARIANT
<222> LOCATION: 20
<223> OTHER INFORMATION: X is A or L
<220> FEATURE:
<221> NAME/KEY: VARIANT
<222> LOCATION: 21
<223> OTHER INFORMATION: X is A or W

<400> SEQUENCE: 78

Ser Gly Ser Xaa Xaa Xaa Xaa Xaa Xaa Xaa Xaa Xaa Xaa Xaa Xaa
 1               5                  10                  15

Xaa Xaa Xaa Xaa Xaa Xaa Xaa Gln Ser Lys Leu
            20                  25

<210> SEQ ID NO 79
<211> LENGTH: 23
<212> TYPE: PRT
<213> ORGANISM: Hepatitis C virus

<400> SEQUENCE: 79

Gln Asp Val Leu Lys Glu Val Lys Ala Ala Ala Ser Lys Val Lys Ala
 1               5                  10                  15

Asn Leu Leu Ser Val Glu Glu
            20

<210> SEQ ID NO 80
<211> LENGTH: 19
<212> TYPE: PRT
<213> ORGANISM: Hepatitis C virus

<400> SEQUENCE: 80

Asp Val Arg Cys His Ala Arg Lys Ala Val Ala His Ile Asn Ser Val
 1               5                  10                  15

Trp Lys Asp

<210> SEQ ID NO 81
<211> LENGTH: 28
<212> TYPE: PRT
<213> ORGANISM: Hepatitis C virus

<400> SEQUENCE: 81

Ile Glu Gln Gly Met Met Leu Ala Glu Gln Phe Lys Gln Lys Ala Leu
 1               5                  10                  15

Gly Leu Leu Gln Thr Ala Ser Arg His Ala Glu Val
            20                  25

<210> SEQ ID NO 82
<211> LENGTH: 17
<212> TYPE: PRT
<213> ORGANISM: Hepatitis C virus
```

```
<220> FEATURE:
<221> NAME/KEY: VARIANT
<222> LOCATION: 1
<223> OTHER INFORMATION: when x is present, x = L
<220> FEATURE:
<221> NAME/KEY:

```
<210> SEQ ID NO 86
<211> LENGTH: 11
<212> TYPE: PRT
<213> ORGANISM: Hepatitis C virus

<400> SEQUENCE: 86

Ser Trp Leu Arg Asp Val Trp Asp Trp Ile Cys
 1               5                  10

<210> SEQ ID NO 87
<211> LENGTH: 28
<212> TYPE: PRT
<213> ORGANISM: Hepatitis C virus

<400> SEQUENCE: 87

Leu Cys Leu Ala Gly Arg Gly Leu Gln Glu Ala Glu Gly Leu Leu
 1               5                  10                  15

Glu Leu Leu Ser Glu His His Pro Leu Leu Asp Val
                20                  25

<210> SEQ ID NO 88
<211> LENGTH: 22
<212> TYPE: PRT
<213> ORGANISM: Hepatitis C virus

<400> SEQUENCE: 88

Glu Leu Gly Phe Gln Pro Gly Leu Lys Val Ala Gln His Leu Ala Tyr
 1               5                  10                  15

Pro Val Pro Asp Val Pro
                20

<210> SEQ ID NO 89
<211> LENGTH: 31
<212> TYPE: PRT
<213> ORGANISM: Hepatitis C virus

<400> SEQUENCE: 89

Ser Gly Ser Trp Leu Arg Asp Val Trp Asp Trp Ile Cys Thr Val Leu
 1               5                  10                  15

Thr Asp Phe Lys Thr Trp Leu Gln Ser Lys Leu Asp Tyr Lys Asp
                20                  25                  30

<210> SEQ ID NO 90
<211> LENGTH: 31
<212> TYPE: PRT
<213> ORGANISM: Hepatitis C virus

<400> SEQUENCE: 90

Ser Gly Ser Trp Leu Arg Asp Asp Trp Asp Trp Glu Cys Thr Val Leu
 1               5                  10                  15

Thr Asp Asp Lys Thr Trp Leu Gln Ser Lys Leu Asp Tyr Lys Asp
                20                  25                  30

<210> SEQ ID NO 91
<211> LENGTH: 27
<212> TYPE: PRT
<213> ORGANISM: Hepatitis C virus

<400> SEQUENCE: 91

Ser Gly Ser Trp Leu Arg Asp Asp Trp Asp Trp Glu Cys Thr Val Leu
 1               5                  10                  15

Thr Asp Asp Lys Thr Trp Leu Gln Ser Lys Leu
                20                  25
```

US 8,728,793 B2

AMPHIPATHIC ALPHA-HELICAL PEPTIDE COMPOSITIONS AS ANTIVIRAL AGENTS

FEDERALLY-SPONSORED RESEARCH OR DEVELOPMENT

This invention was made with Government support under contracts NAG8-1843 awarded by NASA aid DK064223 awarded by the National Institutes of Health. The Government has certain rights in this invention.

CROSS REFERENCE TO RELATED APPLICATIONS

This application claims priority to U.S. Provisional Patent Application No. 60/961,457 filed Jul. 19, 2007, and to U.S. Provisional Patent Application No. 61/080,210 filed Jul. 11, 2008, which applications are incorporated herein by reference in their entirety and for all purposes.

BACKGROUND

HCV is an enveloped positive strand RNA virus. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce structural and non-structural (NS) proteins. In the case of HCV, the generation of mature nonstructural proteins (NS2, NS3, NS4A, NS4B, NS5A, and NS5B) is effected by two viral proteases. The first one is a metalloprotease located in NS2 that cleaves the NS2-NS3 junction in cis; the second one is a serine protease contained within the N-terminal region of NS3 (henceforth referred to as NS3 protease) and mediates all the subsequent cleavages downstream of NS3, both in cis, at the NS3-NS4A cleavage site, and in trans, at the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components.

Among the viral non-structural proteins is NS5A. Inspection of NS5A's amino acid sequence revealed the predicted presence of an amphipathic α-helix (AH) at the $NH_2$-terminus. This AH is necessary and sufficient for mediating membrane association of NS5A and has been proposed to anchor the protein by insertion of the helix within the plane of the membrane. Evidence for a host-cell membrane protein receptor has recently been reported. Genetic disruption of the NS5A AH abrogates NS5A membrane association, and HCV RNA replication is halted.

SUMMARY OF THE INVENTION

The invention features methods and compositions that exploit the ability of amphipathic alpha-helical (AH) peptides to cause disruption of lipid-containing vesicles, such as enveloped viruses, in a size-dependent manner.

Accordingly, in some aspects the disclosure provides methods of inactivating an enveloped virus, the method comprising contacting an enveloped virus having an average particle diameter of less than 250 nm with an amphipathic alpha-helical (AH) peptide in an amount and under conditions effective to facilitate disruption of the viral envelope, with the proviso that the enveloped virus is other than hepatitis C virus (HCV), wherein said contacting is effective to disrupt the viral envelope of the virus, thereby reducing infectivity of the virus. In related embodiments, the enveloped virus is present in a biological fluid, such as blood, and may be extracorporeal.

Examples of conditions effective to facilitate disruption of the viral envelope include a pH of 7.5 or less, a pH of 7.0 or less, a pH of 6.5 or less, a pH of 5.0 or less, a pH of 5.5 or less, a pH of 5.0 or less, a pH of 4.5 or less, or a pH of 4.0 or less.

In additional examples, conditions effective to facilitate disruption of the viral envelope include a temperature of 20° C. or greater, 25° C. or greater, or 30° C. or greater.

Conditions effective to facilitate disruption of the viral envelope can also include can also include contacting the enveloped virus with the AH peptide in a solution with a solute concentration greater than that found in the enveloped virus.

In related embodiments, the disclosure provides methods for treating in vitro or ex vivo biological fluid, comprising contacting an isolated biological fluid with an effective amount of an amphipathic alpha-helical (AH) peptide wherein said contacting provides for disruption of an enveloped virus that may be present in the biological fluid. In some embodiments, the enveloped virus has an average particle diameter of less then 250 nm and is other than hepatitis C virus. In related embodiments, contacting is accomplished by mixing the biological fluid with a composition comprising the AH peptide. In related embodiments, the AH peptide is immobilized on a surface of a substrate.

The disclosure also provide methods for treating a subject having, suspected of having, or susceptible to infection by a enveloped virus, the method comprising administering an amphipathic α-helical (AH) peptide to a subject in need thereof and having, suspected of having, or susceptible to infection by a enveloped virus other than hepatitis C virus, wherein said AH peptide is administered in an amount effective to facilitate disruption of an envelope of an enveloped virus that may be present in the subject or to which the subject may have been or may be exposed.

The disclosure further provides methods for treating a non-human subject having, suspected of having, or susceptible to infection by a enveloped virus, the method comprising: administering an amphipathic α-helical (AH) peptide to a non-human subject in need thereof and having, suspected of having, or susceptible to infection by a enveloped virus, wherein said AH peptide is administered in an amount effective to facilitate disruption of an envelope of an enveloped virus that may be present in the subject or to which the subject may have been or may be exposed.

Also provided are methods for decreasing a level of an enveloped virus contaminating a material, the method comprising treating a material with an effective amount of an amphipathic α-helical (AH) peptide, wherein said treating is effective to disrupt at least 25% of enveloped viral particles that may be associated with the material, wherein the enveloped virus has an average particle diameter of less then 250 nm and is other than hepatitis C virus. The material can be a biological fluid (such as blood or a blood product) or biological tissue (e.g., an organ for transplant), and may be present in a container. The methods can further comprise removing all or a portion of the AH peptide and/or disrupted enveloped viral particle from the material after treating.

The disclosure also provides substrates comprising at least a surface treated with an amphipathic alpha-helical (AH) peptide. The substrate can be, for example, a biological fluid container (e.g., a blood donation bag or bottle), a medical device (e.g., a an in-line filter through which blood or blood product is passed prior to delivery to an individual or through which blood or blood product is passed at the point of collection from an individual), or any variety of other substrates (e.g., a filter, tubing, seal, clamp, transfer leg closure, operating table, or medical examination table). Optionally, the AH peptide is immobilized to a surface of the substrate.

The disclosure further provides disinfectant compositions comprising an amphipathic α-helical (AH) peptide and at least one component that is not pharmaceutically acceptable for human administration.

Other aspects and embodiments will be readily apparent to the ordinarily skilled artisan upon reading the present specification.

BRIEF DESCRIPTION OF THE DRAWINGS

FIG. 2, Panel 2-2, shows analogous experiments to FIG. 2, panel 2-1, except performed on a $TiO_2$ surface.

Figure 1:
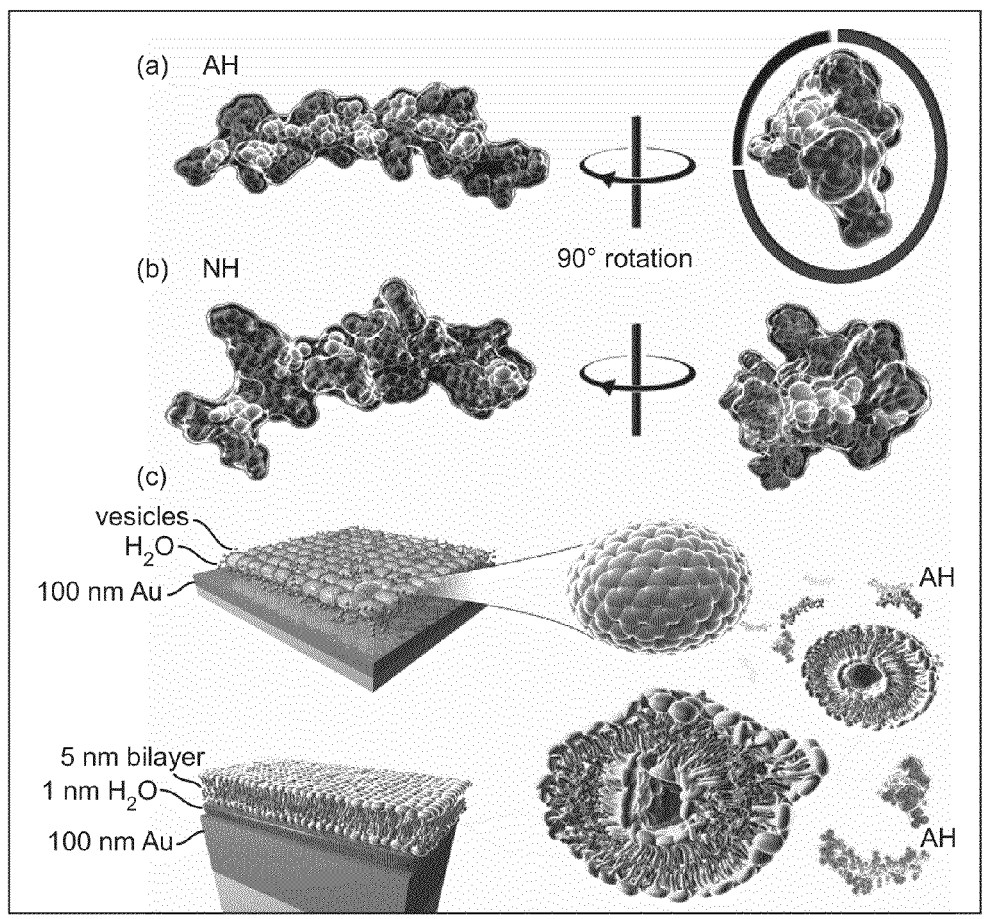
FIG. 1, Panels a-c: Schematic representations of the amphipathic alpha helix (AH) (FIG. 1, panel a) and non-amphipathic, non-helical (NH) (FIG. 1, Panel b) peptides, and proposed schematic of creating bilayer on Au and $TiO_2$ (FIG. 1, panel c).

"Exogenous" in the context of a nucleic acid or polypeptide is used to refer to a nucleic acid or polypeptide that has been introduced into a host cell. "Exogenous" nucleic acids and polypeptides can be native or non-native to the host cell, where an exogenous, native nucleic acid or polypeptide provides for elevated levels of the encoded gene product or polypeptide in the recombinant host cell relative to that found in the host cell prior to introduction of the exogenous molecule.

As used herein, the terms "determining," "measuring," "assessing," and "assaying" are used interchangeably and include both quantitative and qualitative determinations.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, preferably 75% free, and most preferably 90% free from other components with which it is naturally associated.

A "coding sequence" or a sequence that "encodes" a selected polypeptide, is a nucleic acid molecule which is transcribed (in the case of DNA) and translated (in the case of mRNA) into a polypeptide, for example, in-vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a gene product, such as a polypeptide. Where the gene product is a polypeptide, the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Operably linked" refers to an arrangement of elements wherein the components so described are configured so as to perform their usual function. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14 (6):6745-6763 (1986).

An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address located by placing http://www in front of .ncbi.nlm.gov/cgi-bin/BLAST.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., infra; *DNA Cloning*, supra; *Nucleic Acid Hybridization*, supra.

A first polynucleotide is "derived from" a second polynucleotide if it has the same or substantially the same nucleotide sequence as a region of the second polynucleotide, its cDNA, complements thereof, or if it displays sequence identity as described above. This term is not meant to require or imply the polynucleotide must be obtained from the origin cited (although such is encompassed), but rather can be made by any suitable method.

A first polypeptide (or peptide) is "derived from" a second polypeptide (or peptide) if it is (i) encoded by a first polynucleotide derived from a second polynucleotide, or (ii) displays sequence identity to the second polypeptides as described above. This term is not meant to require or imply the polypeptide must be obtained from the origin cited (although such is encompassed), but rather can be made by any suitable method.

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of an AH peptide that can provide for reduction of viral load in an affected subject.

"Subject", "host" and "patient" are used interchangeably herein, to refer to an animal, human or non-human, susceptible to or having an infection by an enveloped pathogen, especially an enveloped virus, and amenable to therapy according to the methods of the invention. Generally, the subject is a mammalian subject, particularly a subject having, suspected of having, or at risk of a viral infection. The methods herein particularly contemplate treatment of a subject having, suspected of having, or at risk of a infection by a virus other than HCV.

DETAILED DESCRIPTION OF EXEMPLARY
EMBODIMENTS OF THE INVENTION

The invention is based on the discovery that amphipathic alpha-helical (AH) peptides rupture lipid vesicles. The efficiency of vesicle rupture mediated by AH peptides is affected by vesicle radius and line tension, with most efficient rupture occurring as the radius decreases and/or the line tension increases. This is postulated to reflect the increased line tension associated with vesicles of smaller radius. The range of vesicle size subject to rupture by the AH peptide encompasses the range of vesicle sizes of a significant number of viruses. Thus, the AH peptide is useful in destruction of viruses extracorporally (e.g., for prevention and disinfection) and within infected individuals (for therapy).

AH Peptides

AH peptides generally have an amino acid sequence based on an amphipathic α-helix of an HCV nonstructural (NS) protein selected from NS5A, NS4B, NS5B, and NS4A, and facilitate disruption of an enveloped virus. Such AH peptides may contain a native (naturally-occurring) amino acid sequence of such NS proteins, including variants that occur in various different HCV genotypes. As describe din more detail below, AH peptides may also be based on such NS proteins, but contain conservative amino acid substitutions which maintain the amphipathic and α-helical nature of the native amino acid sequence.

AH peptides can be of any suitable length, and usually are from about 14 to 30, about 15 to 25, about 16 to 20, about 17 to 20, about 18 to 20 amino acids in length, and can be at least 15, 16, 17, 18, 19, 20, 21, 22, 23, 24, 25, 26, 27, 28, 29, or 30 amino acids in length, with the proviso that the activity of the peptide in viral envelope disruption is maintained. AH peptides also include those that are no more than 30 amino acids, no more than 29, no more than 28 amino acids, no more than 27 amino acids, no more than 26 amino acids, or no more than 25 amino acids in length. AH peptides may be less than 60 amino acids, less than 50 amino acids, less than 30 amino acids, or less than 25 amino acids, with the proviso the peptide is at least about 15 amino acids in length. AH peptides may also be presented in the context of a larger polypeptide, such as a full-length HCV nonstructural polypeptide of NS5A, NS4B, or NS5B or in a fusion polypeptide which contains an AH peptide linked to a heterologous polypeptide.

Exemplary AH peptides include those having an amino acid sequence of the N-terminal amphipathic α-helix of the hepatitis C virus (HCV) nonstructural protein, NS5A. In general such AH peptides contain an amino acid sequence of the formula:

SWLX$_1$X$_2$X$_3$X$_4$X$_5$WX$_6$X$_7$X$_8$X$_9$X$_{10}$ (SEQ ID NO: 1)

wherein:

X$_1$ is charged or polar residue, such as R, H, W, or Y, especially a positively charged residue such as R, K or H;

X$_2$ is any amino acid residue, and can be a residue other than an positively charged residue, e.g., D, I, or T, particularly negatively charged residue such as D or E;

X$_3$ is other than a charged residue, and can be a nonpolar (hydrophobic) residue, such as V or I;

X$_4$ is a nonpolar (hydrophobic) residue, such as W or V;

X$_5$ is a charged (e.g., negatively charged) or polar, uncharged residue, such as D, E, or N, particularly a negatively charged residue such as D or E;

X$_6$ is other than a charged residue, and can be a nonpolar (hydrophobic) residue such as I or V;

X$_7$ is polar, uncharged residue, nonpolar (hydrophobic) residue, or negatively charged residue, such as C or L or E, particularly a polar, uncharged residue, nonpolar (hydrophobic) residue, such as C or L;

X$_8$ is a polar, uncharged residue, a nonpolar (hydrophobic) residue, or a positively charged residue, such as T, S, I, or H, particularly a polar, uncharged residue such as T;

X$_9$ is a nonpolar (hydrophobic) residue, such as V, I or W; and

X$_{10}$ is C or L.

Specific exemplary AH peptides having an exemplary formula of the above, are provided below:

```
SWLRDVWDWICTVL      (SEQ ID NO: 2)
SWLRDVWDWVCTIL      (SEQ ID NO: 3)
SWLRDIWEWVLSIL      (SEQ ID NO: 4)
SWLRIIWDWVCSWC      (SEQ ID NO: 5)
SWLRTIWDWVCSVC      (SEQ ID NO: 6)
SWLHDIWDWVCIVC      (SEQ ID NO: 7)
SWLWDVWDWVLHVL      (SEQ ID NO: 8)
SWLYDIVNWVCTVC      (SEQ ID NO: 9)
SWLRDIWDWVCTVC      (SEQ ID NO: 10)
SWLRDIWDWICEVL      (SEQ ID NO: 11)
```

Exemplary amino acid sequences of NS5A-based AH peptides include those having an amino acid sequence as set out below.

AH Peptides of NS5A

| Genotype | NS Protein | Residues | Amino Acid Sequence |
|---|---|---|---|
| 1a | NS5A | 5-26 | LRDIWDWICEVLSDFKTWLKA (SED ID NO. 12) |
| 1b | NS5A | 4-27 | WLRDVWDWICTVLTDFKTWLQSKL (SEQ ID NO. 13) |
| 2a | NS5A | 4-27 | WLRDVWDWVCTILTDFKNWLTSKL (SEQ ID NO. 14) |
| 2b | NS5A | 4-27 | WLRDIWEWVLSILTDFKNWLSAKL (SEQ ID NO. 15) |
| 3a-K | NS5A | 4-27 | WLRIIWDWVCSVVSDFKTWLSAKI (SEQ ID NO. 16) |
| 3a-NZL | NS5A | 4-27 | WLRTIWDWVCSVLADFKAWLSAKI (SEQ ID NO. 17) |
| 3b | NS5A | 4-27 | WLHDIWDWVCIVLSDFKTWLSAKI (SEQ ID NO. 18) |
| 4a | NS5A | 4-27 | WLWDVWDWVLHVLSDFKTCLKAKF (SEQ ID NO. 19) |
| 10a | NS5A | 4-27 | WLYDIVNWVCTVLADFKLWLGAKI (SEQ ID NO. 20) |
| 11a | NS5A | 4-27 | WLRDIWDWVCTVLSDFRVWLKSKL (SEQ ID NO. 21) |

Further exemplary AH peptides based on NS5A include peptides having an amino acid sequence of:

```
SWLRDVWDWICTVLTDFKTWLQSKL      (SEQ ID NO: 22)
SWLRDVWDWVCTILTDFKNWLTSKL      (SEQ ID NO: 23)
SWLRDIWEWVLSILTDFKNWLSAKL      (SEQ ID NO: 24)
SWLRIIWDWVCSWSDFKTWLSAKI       (SEQ ID NO: 25)
SWLRTIWDWVCSVLADFKAWLSAKI      (SEQ ID NO: 26)
SWLHDIWDWVCIVLSDFKTWLSAKI      (SEQ ID NO: 27)
SWLWDVWDWVLHVLSDFKTCLKAKF      (SEQ ID NO: 28)
SWLYDIVNWVCTVLADFKLWLGAKI      (SEQ ID NO: 29)
SWLRDIWDWVCTVLSDFRVWLKSKL      (SEQ ID NO: 30)
SGSLRDIWDWICEVLSDFKTWLKA       (SEQ ID NO: 31)
SGSWLRDVWDWICTVLTDFKTWLQSKL    (SEQ ID NO: 32)
SGSWLRDVWDWVCTILTDFKNWLTSKL    (SEQ ID NO: 33)
SGSWLRDIWEWVLSILTDFKNWLSAKL    (SEQ ID NO: 34)
SGSWLRIIWDWVCSWSDFKTWLSAKI     (SEQ ID NO: 35)
SGSWLRTIWDWVCSVLADFKAWLSAKI    (SEQ ID NO: 36)
SGSWLHDIWDWVCIVLSDFKTWLSAKI    (SEQ ID NO: 37)
SGSWLWDVWDWVLHVLSDFKTCLKAKF    (SEQ ID NO: 38)
SGSWLYDIVNWVCTVLADFKLWLGAKI    (SEQ ID NO: 39)
SGSWLRDIWDWVCTVLSDFRVWLKSKL    (SEQ ID NO: 40)
GSWLRDVWDWICTVLTDFKTWLQSKL     (SEQ ID NO: 41)
```

-continued

| | |
|---|---|
| GSWLRDVWDWVCTILTDFKNWLTSKL | (SEQ ID NO: 42) |
| GSWLRDIWEWVLSILTDFKNWLSAKL | (SEQ ID NO: 43) |
| GSWLRIIWDWVCSWSDFKTWLSAKI | (SEQ ID NO: 44) |
| GSWLRTIWDWVCSVLADFKAWLSAKI | (SEQ ID NO: 45) |
| GSWLHDIWDWVCIVLSDFKTWLSAKI | (SEQ ID NO: 46) |
| GSWLWDVWDWVLHVLSDFKTCLKAKF | (SEQ ID NO: 47) |
| GSWLYDIVNWVCTVLADFKLWLGAKI | (SEQ ID NO: 48) |
| GSWLRDIWDWVCTVLSDFRVWLKSKL | (SEQ ID NO: 49) |
| SWLRDVWDWICTVLT | (SEQ ID NO: 50) |
| SWLRDVWDWVCTILT | (SEQ ID NO: 51) |
| SWLRDIWEWVLSILT | (SEQ ID NO: 52) |
| SWLRIIWDWVCSWSD | (SEQ ID NO: 53) |
| SWLRTIWDWVCSVLA | (SEQ ID NO: 54) |
| SWLHDIWDWVCIVLS | (SEQ ID NO: 55) |
| SWLWDVWDWVLHVLS | (SEQ ID NO: 56) |
| SWLYDIVNWVCTVLA | (SEQ ID NO: 57) |
| SWLRDIWDWVCTVLS | (SEQ ID NO: 58) |
| SWLRDVWDWICTVLTD | (SEQ ID NO: 59) |
| SWLRDIWEWVLSILTD | (SEQ ID NO: 60) |
| SWLRDIWEWVLSILTD | (SEQ ID NO: 61) |
| SWLRIIWDWVCSWSDF | (SEQ ID NO: 62) |
| SWLRTIWDWVCSVLAD | (SEQ ID NO: 63) |
| SWLHDIWDWVCIVLSD | (SEQ ID NO: 64) |
| SWLWDVWDWVLHVLSD | (SEQ ID NO: 65) |
| SWLYDIVNWVCTVLAD | (SEQ ID NO: 66) |
| SWLRDIWDWVCTVLSD | (SEQ ID NO: 67) |
| SWLRDVWDWICTVLTDF | (SEQ ID NO: 68) |
| SWLRDVWDWVCTILTDF | (SEQ ID NO: 69) |
| SWLRDIWEWVLSILTDF | (SEQ ID NO: 70) |
| SWLRIIWDWVCSWSKFK | (SEQ ID NO: 71) |
| SWLRTIWDWVCSVLADF | (SEQ ID NO: 72) |
| SWLHDIWDWVCIVLSDF | (SEQ ID NO: 73) |
| SWLWDVWDWVLHVLSDF | (SEQ ID NO: 74) |
| SWLYDIVNWVCTVLADF | (SEQ ID NO: 75) |
| SWLRDIWDWVCTVLSDF | (SEQ ID NO: 76) |

A specific exemplary AH peptide having an NS5A amino acid sequence is:

| | |
|---|---|
| SGSWLRD<u>V</u>WDW<u>I</u>CTVLTD<u>F</u>KTWLQSKLDYK | (SEQ ID NO: 77) |

Notably, substitution of the hydrophobic residues underlined in the sequence immediately above with charged amino acids (D, E, and D, respectively), provide no sustained hydrophobic patch and resulted in a decrease in activity in vesicle disruption.

Further exemplary AH peptides include peptides having an amino acid sequence of SGSWLRDVWDWICTVLTDFK-TWLQSKL (SEQ ID NO: 32) except that the exemplary AH peptides have one or more of the following amino acid substitutions relative to SEQ ID NO: 32: substitution of L at amino acid position 16 by A or K; or substitution of T at amino acid position 17 by A; or substitution of D at amino acid position 18 by A; or substitution of F at amino acid position 19 by A; or substitution of K at amino acid position 20 by A; or substitution of W at amino acid position 22 by A; or substitution of L at amino acid position 23 by K.

Still further exemplary AH peptides include peptides having an amino acid sequence of:

$$\text{SGSX}_1\text{X}_2\text{X}_3\text{X}_4\text{X}_5\text{X}_6\text{X}_7\text{X}_8\text{X}_9\text{X}_{10}\text{X}_{11}\text{X}_{12}\text{X}_{13}\text{X}_{14}\text{X}_{15}\text{X}_{16}\text{X}_{17}\text{X}_{18}$$ (SEQ ID NO: 78)
$$\text{X}_{19}\text{X}_{20}\text{QSKL},$$

wherein $X_1$ is A or F; $X_2$ is A or K; $X_3$ is A or N; $X_4$ is A or S; $X_5$ is D, I or S; $X_6$ is A or F; $X_7$ is A or S; $X_8$ is A or F; $X_9$ is E or L; $X_{10}$ is A or S; $X_{11}$ is A, E or W; $X_{12}$ is D or S; $X_{13}$ is A or K; $X_{14}$ is A, S or W; $X_{15}$ is A or S; $X_{16}$ is D or L; $X_{17}$ is A or L; $X_{18}$ is A or W; $X_{19}$ is A or F; and $X_{20}$ is A or K.

AH peptides can also be based on an amphipathic α-helical amino acid sequence of HCV NS5B, which is exemplified by the amino acid sequences:

| | |
|---|---|
| QDVLKEVKAAASKVKANLLSVEE | (SEQ ID NO: 79) |
| DVRCHARKAVAHINSVWKD | (SEQ ID NO: 80) |

AH peptides can also be based on an amphipathic α-helical amino acid sequence of HCV NS4B, which is exemplified by the amino acid sequence:

| | |
|---|---|
| IEQGMMLAEQFKQKALGLLQTASRHAEV | (SEQ ID NO: 81) |

Further AH peptides can also contain an amino acid sequence of the formula:

| | |
|---|---|
| $X_1X_2\text{DVWDWICTX}_3X_4X_5X_6X_7X_8X_9$, | (SEQ ID NO: 82) | with the proviso that when $X_1$ and $X_2$ are present, $X_1$ is L and $X_2$ is R; wherein when $X_1$ and $X_2$ are present, X3, X4, X5, X6, X7, X8 and X9 are optionally present, and when $X_3$, $X_4$, $X_5$, $X_6$, $X_7$, $X_8$ and $X_9$ are present, $X_3$ is V, $X_4$ is L, $X_5$ is T, $X_6$ is D, $X_7$ is F, $X_8$ is K and $X_9$ is T; and wherein when $X_6$ is present, $X_3$, $X_4$ and $X_5$ are all present, and $X_6$ is D, $X_3$ is V, $X_4$ is L, and $X_5$ is T.

Exemplary AH peptides include those containing an amino acid sequence of:

| | |
|---|---|
| LRDVWDWICTVLTDFKT; | (SEQ ID NO: 83) |
| LRDVWDWICT; | (SEQ ID NO: 84) |

```
DVWDWICTVLTD;                        (SEQ ID NO: 85)

SWLRDVWDWIC;                         (SEQ ID NO: 86)

LCLAGRGLQEAEGLLLELLSEHHPLLDV         (SEQ ID NO: 87)
or a fragment of 6 to 27 amino
acids thereof;
or ELGFQPGLKVAQHLAYPVPDVP               (SEQ ID NO: 88)
or a fragment of 6 to 21 amino
acids thereof.
```

Other AH peptides include those described in WO 2002/088731 and US 2004/0265792, which are incorporated herein by reference with respect to the disclosure of such peptides.

AH peptides suitable for use in disruption of viral envelopes, including variants (e.g., natural, recombinant, or synthetic variants) of naturally-occurring AH peptides can be identified by, for example, modeling of the structure a selected peptide after the structure of an AH peptide having a naturally-occurring amino acid sequence of an amphipathic α-helix of an HCV NS protein, such as NS5A. Appropriate amphipathic and/or α-helical properties of such peptides can be assessed by a variety of different techniques, such as circular dichroism measurements. Activity in disruption of an enveloped virus can be assessed in an in vitro assay using a viral culture or using the lipid vesicle assay described in the Examples below.

The amino acid sequences and three-dimensional structure of amphipathic α-helical peptides are well understood in the art. The ordinarily skilled artisan can readily generate variants of the AH peptide amino acid sequences described herein. For example, such substitutions can be made so that they are spaced at intervals along the predicted α-helix such that an α-helical structure with a hydrophobic face and a hydrophilic face is maintained. Thus AH peptide variants that retain activity in disruption of a viral envelope that have, for example, conservative amino acid substitutions relative to a naturally-occurring AH peptide amino acid sequence so as to result in replacement of amino acid residues of an AH peptide with residues that provide for similar charge, polarity, and retain the α-helical structure can be readily generated.

It is appreciated that certain amino acid substitutions can result in peptides can disrupt the formation of the helix; however, the nature of these substitutions is already understood by those of ordinary skill and can be avoided, or purposefully used, as desired. Insertion of, for example, disruptive proline residues, can be undesirable. Thus, it is well within ordinary skill to substitute one or more amino acids in these sequences to obtain AH peptides that retain the desired activity in disrupting viral envelopes.

AH peptides can have residues linked by native amide bonds or by non-native bonds. Reference to "peptide" herein is meant to encompass both a polymer of amino acids linked by a native amide bonds or non-native amide bonds.

It should be understood that as used throughout, and unless specifically indicated otherwise, the term "amino acid" is used herein in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, p-alanine, ornithine, etc.; and chemically synthesized compounds having properties known in the art to be characteristic of amino acids. As used herein, the term "proteogenic" indicates that the amino acid can be incorporated into a peptide, polypeptide, or protein in a cell through a metabolic pathway.

The incorporation of non-natural amino acids, including synthetic non-native amino acids, substituted amino acids, or one or more D-amino acids into the present AH peptides can provide for, for example, increased stability in vitro or in vivo (e.g., D-amino acid-containing peptides as compared to L-amino acid-containing peptides). For example, AH peptides incorporating 1, 2, 3, 4, 5, 6, 7, 8, 9, 10 or more D-amino acids can be particularly useful when greater stability (e.g., in an in vivo setting) is desired or required. For example, D-amino acid-containing peptides can be provided that are resistant to peptidases and proteases, thereby providing improved bioavailability of the molecule, and prolonged lifetimes in vivo and in vitro when such properties are desirable. Moreover, D-amino acid-containing peptides are not efficiently processed for major histocompatibility complex class 11-restricted presentation to T helper cells, and are therefore less likely to induce humoral immune responses in the whole organism than purely L-amino acid-containing peptides.

Selection of amino acid residues for use in an AH peptide, particularly one based on a naturally-occurring amphipathic, α-helical amino acid sequence (e.g., of NS5A), can take into consideration the hydropathic index of the amino acid present in the reference sequence and the hydropathic index of the amino acid residue proposed for substitution. The importance of the hydropathic amino acid index in conferring interactive biological action on a protein has been discussed by Kyte and Doolittle (1982, J. Mol. Biol., 157: 105-132). It is accepted that the relative hydropathic character of amino acids contributes to the secondary structure of the resultant protein. This, in turn, affects the interaction of the protein with other molecules.

Based on its amphipathic characteristics, which are influenced by polarity and charge, each amino acid has been assigned a hydropathic index as follows: isoleucine (+4.5); valine (+4.2); leucine (+3.8); phenylalanine (+2.8); cysteinel-cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

Certain amino acids in a peptide, polypeptide, or protein can be substituted for other amino acids having a similar hydropathic index or score and produce a resultant peptide, etc., having similar biological activity, i.e., which still retains biological functionality in disrupting viral envelopes. In making such changes, amino acids having hydropathic indices within ±2 can generally be substituted for one another. Exemplary suitable substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101, herein incorporated by reference, discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (t−0.3); asparagine/glutamine (+0.2); glycine (0); threonine (−0.4); proline (−0.5 1-1); alanine/histidine (−0.5); cysteine (−1.0); methionine (−1.3);

valine (−1.5); leucine/isoleucine (−1.8); tyrosine (−2.3); phenylalanine (−2.5); and tryptophan (−3.4). Thus, one amino acid in a reference amino acid sequence can be substituted by another amino acid having a similar hydrophilicity score and still be expected to provide a peptide having similar biological activity, e.g., retaining activity in disrupting viral envelopes. In making such changes, amino acids having hydropathic indices within 1-2 are substituted for one another, those within ±1 being of interest, and those within ±0.5 more usual.

As outlined above, amino acid substitutions in the AH peptides can be based on the relative similarity of the amino acid side-chain substituents, for example, their hydrophobicity, hydrophilicity, charge, size, etc.

Exemplary substitutions that take various of the foregoing characteristics into consideration in order to produce conservative amino acid changes resulting in AH peptides having changes that do not substantially affect activity in disrupting viral envelopes can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine.

The AH peptides can be provided in the context of the nonstructural protein or fragment thereof or can be provided in the form of a fusion protein between an AH peptide and a heterologous polypeptide. For example, the AH peptide can be provided as a fusion protein that contains a detectable label, such as a fluorescent polypeptide (e.g., green fluorescent protein) or an immunodetectable label (e.g., FLAG, which can be exploited to facilitate isolation by immunoisolation techniques). In other examples of AH peptide-containing fusion proteins, the heterologous polypeptide can be a virucidal peptide, a lipid binding protein (e.g., to facilitate clearance of lipids that may be by-products of disruption of viral envelopes, a polypeptide that enhances serum half-life (e.g., by increasing the size of the molecule, such as a PEGylated polypeptide), an antibody or antigen binding fragment thereof; or a polypeptide that facilitates recombinant production and/or isolation. Such AH peptide fusion proteins may include a spacer between the AH peptide amino acid sequence and the amino acid sequence of the heterologous polypeptide (e.g., to facilitate presentation of the amphipathic α-helix to viral envelopes).

Methods of Making AH Peptides

AH peptides can be produced according to any of a variety of methods known in the art, including recombinant and synthetic methods. AH peptides that are relatively short (e.g., 50 residues or less) can generally be produced by suitable synthetic methods well known in the art.

Since the genetic code and recombinant techniques for manipulating nucleic acid are known, and the amino acid sequences of AH peptides are exemplified above, the design and recombinant production of nucleic acids suitable for recombinant production of an AH peptide is well within the skill of an artisan. For example, standard recombinant DNA technology (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.) methods can be used to obtain (e.g., by isolating nucleic acid encoding an HCV polypeptide containing an AH peptide from a library of nucleic acids using any one or a combination of a variety of recombinant methods (e.g., PCR)). Where modification is desired, e.g., to subclone an AH peptide-containing sequence, to provide for conservative amino acid substitutions, etc.) site directed mutagenesis, PCR and other techniques can be used. Nucleic acids encoding an AH peptide may also be made by chemical synthesis entirely from oligonucleotides.

AH peptide-encoding constructs can be introduced into an appropriate host cell, where, when desired, the construct provides for a suitable operably linked promoter to provide for expression in the host cell (where such constructs are referred to as expression vectors). The constructs can be maintained as an episomal element or provide for host cell genomic integration. In this latter aspect, the AH peptide coding sequence may be In some embodiments, the constructs are simply to provide for production of additional construct DNA material, and thus in such embodiments need only provide for replication in the host cell. Constructs that facilitate genomic integration may provide for insertion of the AH peptide coding sequence adjacent a host cell promoter, or may provide for integration of a promoter-AH peptide expression cassette. Constructs may optionally contain one or more selection markers, e.g., tetracycline or neomycin, to permit detection of those cells transformed with the desired DNA sequences. Exemplary vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used. Expression constructs can further include 3' and 5' untranslated regions (UTRs) which may direct RNA stability, translational efficiency; transcriptional terminators, and other elements that facilitate transcription and/or translation in a host cell. Constructs may also contain restriction sites, multiple cloning sites, primer binding sites, ligatable ends, recombination sites etc., usually in order to facilitate the construction of a nucleic acid encoding a polypeptide of interest.

Promoters are selected according to the host cell in which expression is desired. Eukaryotic promoters can be any promoter that is functional in a eukaryotic host cell, including viral promoters and promoters derived from eukaryotic genes. Exemplary eukaryotic promoters can include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

Host cells for production of AH peptide-encoding constructs and/or production of AH peptides can be selected from a variety of different host cells known in the art. Exemplary host cells include prokaryotic and eukaryotic host cells, including bacterial, yeast, and mammalian host cells (e.g., cultured mammalian cell lines).

Viruses Susceptible to Disruption by AH Peptides

AH peptides effect viral envelope disruption, which serves to inhibit viral infection, inhibit viral replication (e.g., due to reduced viruses to provide for infection), reduce viral load (e.g., by decreasing the relative amount of infective viral particles), reduce infectivity (e.g., as in the context of a virally contaminated surface), and the like.

As discussed in the Examples, the efficacy in AH peptides in effecting viral envelope disruption is inversely proportional to enveloped viral particle size and directly proportional to line tension. Stated differently, as the viral particle size (e.g., as measured by particle diameter or radius) increases, the efficiency of AH peptides disclosed herein to provide for disruption of the enveloped virus decreases. As the line tension of an enveloped viral particle increases, the efficiency of AH peptides in disrupting the enveloped viral particle increase. For example, as illustrated with the AH peptide exemplified in the Examples, while a population of vesicles of about 58 nm average diameter were disrupted such that no detectable intact vesicles were detected (100% disruption). In general particles having an average diameter of 25 nm to 90 nm were disrupted such that no detectable intact vesicles were detected (100% disruption). In contrast, when an exemplary AH peptide was contacted with a population of vesicles of about 148 nm average diameter, about 75% were disrupted. It should be noted that while the efficiency of disruption will be decreased with increasing enveloped virus particle size, this is not to say the AH peptides would not be useful in "killing" such viruses. To the contrary, in the context of in vivo therapy, a reduction in viral load can serve to provide for a level of viral infection that can be better handled by the immune system of the host. In addition, AH peptide-based therapies can be use in conjunction with other antiviral therapies to provide for more complete viral inhibition. Similarly in the context of extracorporeal use, AH peptides can be used in conjunction with other virucidal agents to provide for acceptable levels of infectious virus.

For example, in the context of AH peptides based on the amphipathic α-helix of NS5A polypeptide, a population of vesicles an average diameter of about 50 nm were disrupted so that no detectable intact vesicle remained, with vesicles having an average diameter of 25 nm to 90 nm also being "completely" disrupted while a population of vesicles having an average diameter of about 148 nm were about 75% disrupted. The methods thus contemplate use of AH peptides to provide for disruption of about 20%, 25%, 30%, 35%, 40%, 45%, 50%, 55%, 60%, 65%, 70%, 75%, 80%, 85%, 90%, 95%, or 99% or greater up to 100% of enveloped virions in a population of enveloped virions. It is noted that even at low levels of disruption, the AH peptides can be useful when used in conjunction with a second antiviral agent (e.g., a second disinfectant or second antiviral therapeutic).

Thus the present disclosure contemplates methods in which the AH peptides disclosed herein are used to disrupt enveloped viruses having an average particle diameter of less than 250 nm, 200 nm, or 150 nm, with enveloped viruses having an average particle diameter of less than 110 nm, 100 nm, 95 nm, 90 nm, 85 nm, 80 nm, 75 nm, 70 nm, 65 nm, 60 nm, 55 nm, 50 nm, 45 nm, or 40 nm in diameter. Notably, the size of particles susceptible to disruption by AH peptides disclosed herein is much smaller than the size of, for example, human red blood cells which are on the order of microns in diameter. Thus the AH peptides may provide for antiviral activity without disruption of human red blood cells, human immune cells (e.g., T cells, B cells, macrophages, neutrophils, eosinophils, etc.), or other host cells, thus avoiding or reducing side effects (e.g., anemia, leucopenia, immunosuppression, etc.).

In specific embodiments of the methods disclosed herein, the disclosed AH peptides are used to disrupt enveloped viruses having an average particle diameter greater than about 80 nm in diameter and less than about 250 nm in diameter. For example, in some embodiments the disclosed AH peptides are used to disrupt enveloped viruses having an average particle diameter greater than about 90 nm in diameter and less than about 250 nm in diameter, greater than about 100 nm in diameter and less than about 250 nm in diameter, greater than about 110 nm in diameter and less than about 250 nm in diameter, greater than about 120 nm in diameter and less than about 250 nm in diameter, greater than about 130 nm in diameter and less than about 250 nm in diameter, greater than about 140 nm in diameter and less than about 250 nm in diameter, greater than about 150 nm in diameter and less than about 250 nm in diameter, greater than about 160 nm in diameter and less than about 250 nm in diameter, greater than about 170 nm in diameter and less than about 250 nm in diameter, greater than about 180 nm in diameter and less than about 250 nm in diameter, greater than about 190 nm in diameter and less than about 250 nm in diameter, greater than about 200 nm in diameter and less than about 250 nm in diameter, greater than about 210 nm in diameter and less than about 250 nm in diameter, greater than about 220 nm in diameter and less than about 250 nm in diameter, greater than about 230 nm in diameter and less than about 250 nm in diameter, or greater than about 240 nm in diameter and less than about 250 nm in diameter. In one embodiment, the enveloped virus to be disrupted using an AH peptide has an average particle diameter of less than about 250 nm but does not have an average particle diameter of about 25 nm to about 80 nm in diameter.

Exemplary enveloped viruses that can be suitable to be disrupted using the AH peptides disclosed herein include (from roughly larger to smaller particle diameter) poxvirus (about 170-200 nm×300-450 nm average particle diameter), baculovirus (about 60 nm×300 nm size average particle diameter), paramyxoviruses (about 150-300 nm average particle diameter), arenaviruses (about 50-300 nm average particle diameter), herpesviruses (about 150-200 nm average particle diameter, e.g., HSV (e.g., HSV1, HSV2), CMV, EBV, etc.), orthomyxoviruses (about 90-120 nm average particle diameter), bunya viruses (about 90-120 nm average particle diameter), coronaviruses (about 80-160 nm average particle diameter), retroviruses (about 80-100 nm average particle diameter; e.g., HIV), togaviruses (about 60-70 nm average particle diameter), and flaviviruses (about 40-50 nm average particle diameter), and hepadnaviruses (about 42 nm average particle diameter, e.g., HBV). In one embodiment, the virus to be disrupted using an AH peptide is other than an HCV virus.

Susceptibility of enveloped viruses to disruption by AH peptides can also be assessed by line tension. Enveloped viral particles having a line tension of greater than from about 10-12 Newtons (N) to about 10-14 Newtons have increased susceptibility to disruption by AH peptides, while enveloped viral particles having a line tension of less than these values are generally less susceptible to disruption.

Diseases Susceptible to Treatment Using AH Peptides

Diseases susceptible to treatment using one or more of the AH peptides disclosed herein include, but are not limited to, diseases caused by infection of a host with one or more of the above viruses. For example, the peptides disclosed herein may be used to treat disease caused by one or more of the following viruses: poxvirus, baculovirus, paramyxoviruses, arenaviruses, herpesviruses (e.g., HSV (e.g., HSV1, HSV2), CMV, EBV, etc.), orthomyxoviruses, bunya viruses, coronaviruses, retroviruses (e.g., HIV), togaviruses, flaviviruses and hepadnaviruses. In one embodiment, the disease to be treated using an AH peptide is other than one caused by an HCV virus.

Exemplary diseases that may be caused by one or more of the above viruses and which may be susceptible to treatment using one or more of the AH peptides disclosed herein include small pox, mumps, measles, bronchiolitis, pneumonia, respiratory tract disease, croup, bronchitis, phocine distemper virus, Newcastle disease, hemorrhagic fevers (e.g., Bolivian, Argentine, Brazilian, Venezuelan, and Lassa hemorrhagic fevers), mucocutaneous infection as a result of infection with herpes virus, gingivostomatitis, herpes labialis, genital herpes, herpes simplex keratitis, neonatal herpes simplex, encephalitis resulting from infection with herpes virus, influenza, Rift Valley Fever, Sandfly Fever, California Encephalitis, Oropouche Fever, Crimean-Congo Hemorrhagic Fever, Sin Nombre Virus/Four Corner's Disease, Hemorrhagic Fever with Renal Syndrome, severe acute respiratory syndrome (SARS), enzootic bovine leukosis, equine infectious anaemia and caprine arthritis-encephalitis, Acquired Immune Deficiency Syndrome (AIDS), Chikungunya, Eastern and Western Equine Encephalitis, Venezuelan Equine Encephalitis, St. Louis Encephalitis, West Nile Encephalitis, Yellow fever, Dengue fever and Dengue Hemorrhagic fever, and liver infection caused by hepadnavirus infection.

AH Peptide Formulations

AH peptides will generally be formulated in accordance with the use to which the AH peptides will be applied. Formulations generally contain AH peptides at a concentration suitable for the purpose to which the formulation is to be applied (e.g., disinfectant, therapy).

The AH peptides, or AH peptide compositions, may comprise, consist essentially of, or consist of the peptide sequences, or AH peptides, disclosed herein. The phrase "consists essentially of or consisting essentially of" or the like, when applied to AH peptides refers to peptide sequences like those disclosed herein, but which contain additional amino acids (or analogs or derivatives thereof as discussed above). Such additional amino acids, etc., however, do not materially affect the basic and novel characteristic(s) of these peptides in disrupting viral envelopes.

AH peptide formulations can contain 2, 3, 4, 5, or more different AH peptides, and may further contain components that provide for stability of the peptide in solution.

AH peptide formulations can be provided so as to facilitate efficient lysis of enveloped virus by the AH peptide. One or more AH peptide formulation parameters that can be modulated so as to provide for enhanced AH peptide-mediated lysis include, but are not necessarily limited to, concentration of AH peptide, pH, and osmolality. For example, an AH peptide formulation having a pH of 7.5 or less may be utilized, e.g., a pH of about 7.0, about 6.5, about 6.0, about 5.5, about 5.0, about 4.5, or about 4.0. The concentration of the AH peptide in the formulation can also be adjusted to facilitate efficient lysis of enveloped virus. For example, concentrations of about 1 µM, 2 µM, 3 µM, 4 µM, 5 µM, 6 µM, 7 µM, 8 µM, 9 µM, 10 µM, 11 µM, 12 µM, 13 µM, 14 µM, or 15 µM can be utilized in an AH peptide formulation. The osmolality of the formulation can also be adjusted so as to facilitate efficient lysis of enveloped virus by the AH peptide. For example, the concentration of one or more salts in an AH peptide formulation can be adjusted such that an osmotic pressure equivalent to that of a solution with a NaCl concentration of about 100 mM, about 150 mM, about 200 mM, about 250 mM, about 300 mM, about 350 mM, about 400 mM, about 450 mM, about 500 mM, 550 mM, or about 600 mM is achieved. AH peptide formulations include those that provide for a microenvironment at the site of delivery that reflects one or more of these formulation parameters. It should be understood that benefit provided by the adjustment of one or more of the above parameters may depend on one or more of the other parameters. For example, as indicated in the Examples the benefit provided by adjusting pH or osmolality may depend on the concentration of AH peptide used in the formulation.

Formulations for Use in as General Virucidal Disinfectant Composition

AH peptides can be provided in formulations suitable for use as a disinfectant. Because such formulations are useful in contexts that do not involve administration to a subject, such antiviral formulations can contain a carrier which is other than a pharmaceutically acceptable carrier suitable for human administration. Where the formulations are used to treat a biological fluid (e.g., blood) which is then to be administered to a subject, the AH peptides should be formulated so that they contain a pharmaceutically acceptable carrier or have levels of otherwise non-pharmaceutically acceptable components that are sufficiently diluted in the biological fluid or tissue to be treated to that the are non-toxic to the subject receiving the biological fluid or tissue.

Suitable diluents for such AH peptide formulations include any of a number of compounds used in the preparation of isotonic solutions. Exemplary solutes include but are not limited to sugars such as dextrose and glucose, polysaccharides such as dextran, albumin, and salts of alkali earth metals including sodium chloride, potassium chloride, and potassium bromide. Exemplary combinations of solutes known for their utility in storing peptides can also be suitable and include, without limitation, such combinations as citrate-phosphate-dextrose, citrate-phosphate-dextrose-adenine, and saline-mannitol-dextrose-adenine.

Diluents having utility in the practice of the present methods for their isotonic characteristics can be combined. Combining diluents is particularly suitable when disinfecting red blood cells because commercial collective units of red blood cells are frequently stored in isotonic solutions containing anti-coagulant, such as ACID (acid-citrate-dextrose), CPD (citrate-phosphate-dextrose), CPD-A (CPD-adenine). Thus, when disinfecting collective units of red blood cells stored in isotonic solutions of anti-coagulant, the disinfectant composition may be prepared in a different isotonic diluent, e.g., normal saline, and combined with the anti-coagulant solution.

As noted above, the AH peptides can be formulated so as to facilitate efficient lysis of enveloped virus by the AH peptide. In the context of use of AH peptide formulations as general virucidal disinfectants, AH peptide formulation parameters can be modulated so as to provide an AH peptide formulation having, for example, a pH of 7.5 or less, e.g., a pH of about 7.0, about 6.5, about 6.0, about 5.5, about 5.0, about 4.5, or about 4.0. The concentration of the AH peptide in the formulation can also be adjusted to facilitate efficient lysis of enveloped virus. For example, concentrations of about 1 µM, 2 µM, 3 µM, 4 µM, 5 µM, 6 µM, 7 µM, 8 µM, 9 µM, 10 µM, 11 µM, 12 µM, 13 µM, 14 µM, or 15 µM can be utilized in an AH peptide formulation. The osmolality of the formulation can also be adjusted so as to facilitate efficient lysis of enveloped virus by the AH peptide. For example, the concentration of one or more salts in an AH peptide formulation can be adjusted such that an osmotic pressure equivalent to that of a solution with a NaCl concentration of about 100 mM, about 150 mM, about 200 mM, about 250 mM, about 300 mM, about 350 mM, about 400 mM, about 450 mM, about 500 mM, 550 mM, or about 600 mM is achieved. AH peptide formulations include those that provide for a microenvironment at the site of delivery that reflects one or more of these formulation parameters. It should be understood that benefit provided by the adjustment of one or more of the above parameters may depend on one or more of the other parameters. For example, as indicated in the Examples the benefit provided by adjusting pH or osmolality may depend on the concentration of AH peptide used in the formulation.

Formulations for Antiviral Therapy

AH peptides can be formulated for therapy in humans or non-humans in accordance with known methods compatible with peptide drugs, and which maintain the activity of the AH peptide in disrupting viral envelopes of enveloped viruses having a diameter of less than about 250 nm.

As noted above, the AH peptides can be formulated so as to facilitate efficient lysis of enveloped virus by the AH peptide. In the context of use of AH peptide formulations in antiviral therapy, the AH peptide formulation parameters should provide for a formulation that remains suitable for administration to a host according to the desired route of administration. For example, a topical AH peptide formulation can be modified with respect to pH (e.g., a pH below pH 7.5). AH peptide formulation parameters that can be modulated so as to provide an AH peptide formulation suitable for use in a therapy include, but are not necessarily limited to concentration of AH peptide, pH, and osmolality. For example, an AH peptide formulation having a pH of 7.5 or less may be utilized, e.g., a pH of about 7.0, about 6.5, about 6.0, about 5.5, about 5.0, about 4.5, or about 4.0. The concentration of the AH peptide in the formulation can also be adjusted to facilitate efficient lysis of enveloped virus. For example, concentrations of about 1 µM, 2 µM, 3 µM, 4 µM, 5 µM, 6 µM, 7 µM, 8 µM, 9 µM, 10 µM, 11 µM, 12 µM, 13 µM, 14 µM, or 15 µM can be utilized in an AH peptide formulation. The osmolality of the formulation can also be adjusted so as to facilitate efficient lysis of enveloped virus by the AH peptide. For example, the concentration of one or more salts in an AH peptide formulation can be adjusted such that an osmotic pressure equivalent to that of a solution with a NaCl concentration of about 100 mM, about 150 mM, about 200 mM, about 250 mM, about 300 mM, about 350 mM, about 400 mM, about 450 mM, about 500 mM, 550 mM, or about 600 mM is achieved. AH peptide formulations include those that provide for a microenvironment at the site of delivery that reflects one or more of these formulation parameters. It should be understood that benefit provided by the adjustment of one or more of the above parameters may depend on one or more of the other parameters. For example, as indicated in the Examples the benefit provided by adjusting pH or osmolality may depend on the concentration of AH peptide used in the formulation.

AH peptides, e.g., in the form of a pharmaceutically acceptable salt, can be formulated for oral, topical or parenteral administration for use in the methods disclosed herein. In certain embodiments, e.g., where an AH peptide is administered as a liquid injectable (such as in those embodiments where they are administered intravenously or directly into a tissue), an AH peptide formulation is provided as a ready-to-use dosage form, or as a reconstitutable storage-stable powder or liquid composed of pharmaceutically acceptable carriers and excipients.

Methods for producing and formulating AH peptides suitable for administration to a subject (e.g., a human subject) are well known in the art. For example, AH peptides can be provided in a pharmaceutical composition comprising an effective amount of an AH peptide and a pharmaceutical excipients (e.g., saline). The pharmaceutical composition may optionally include other additives (e.g., buffers, stabilizers, preservatives, and the like). An effective amount of AH peptide is generally an amount effective to provide for enhancing an antiviral effect in a subject for a desired period. A therapeutic goal (e.g., reduction in viral load) can be accomplished by single or multiple doses under varying dosing regimen.

By way of illustration, the AH peptide compositions can be admixed with conventional pharmaceutically acceptable carriers and excipients (i.e., vehicles) and used in the form of aqueous solutions, tablets, capsules, elixirs, suspensions, syrups, wafers, patches and the like. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in pharmaceutical formulations include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener. A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. Additionally, it may be desirable to add a coloring agent to make the dosage form more attractive in appearance or to help identify the product.

AH peptides and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an antioxidant, for example, sodium metabisulphite may be included in the formulation. Alternatively, the solution can be freeze dried and then reconstituted with a suitable solvent just prior to administration.

AH peptides and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

AH peptides and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of AH peptides in controlled amounts. The construction and use of transdermal patches for the delivery of pharmaceutical agents is well known in the art. See, e.g., U.S. Pat. No. 5,023,252, herein incorporated by reference in its entirety. Such patches may be constructed for continuous, pulsatile, or on demand delivery of pharmaceutical agents.

In certain embodiments of interest, the AH peptide composition is administered as a single pharmaceutical formulation. It also may be administered with an effective amount of another agent that includes other suitable compounds and carriers, and also may be used in combination with other active agents. The present disclosure thus provide pharmaceutically acceptable AH peptide compositions comprising pharmaceutically acceptable excipients. The pharmaceutically acceptable excipients include, for example, any suitable vehicles, adjuvants, carriers or diluents, and are readily available to the public. The pharmaceutical compositions may further contain other active agents as are well known in the art.

One skilled in the art will appreciate that a variety of suitable methods of administering a formulation of AH peptide to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of AH peptides. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

AH peptide formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams. Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of AH peptide calculated in an amount sufficient to produce the desired effect in association with a pharmaceutically acceptable diluent, carrier or vehicle. The specifications for the novel unit dosage forms of AH peptide depend on the particular compound employed and the effect to be achieved, and the pharmacodynamics associated with each compound in the host. Those of skill in the art will readily appreciate that dose levels can vary as a function of the specific compound, the nature of the delivery vehicle, and the like. Suitable dosages for a given compound are readily determinable by those of skill in the art by a variety of means.

Optionally, the pharmaceutical composition may contain other pharmaceutically acceptable components, such a buffers, surfactants, antioxidants, viscosity modifying agents, preservatives and the like. Each of these components is well-known in the art. See, e.g., U.S. Pat. No. 5,985,310, the disclosure of which is herein incorporated by reference.

Other components suitable for use in the AH peptide formulations can be found in Remington's Pharmaceutical Sciences, Mack Pub. Co., 18th edition (June 1995). In an embodiment, the aqueous cyclodextrin solution further comprise dextrose, e.g., about 5% dextrose.

Methods of Use

The AH peptides can be used in a variety of settings both in vivo and in vitro to provide for disruption of enveloped viruses.

The terms "an effective amount" (or, in the context of a therapy, a "pharmaceutically effective amount") of an AH peptide generally refers to an amount of AH peptide, or combinations of AH peptides, effective to facilitate disruption of viral envelopes to provide for a reducing in infectious viral particles, e.g., to provide for disinfecting a surface; reducing viral load in an infected subject; reducing or ameliorating conditions, symptoms, or disorders associated with viral infection in an affected subject; and the like.

Effective amounts of AH peptides, suitable delivery vehicles, and protocols can be determined by conventional means. For example, in the context of therapy a medical practitioner can commence treatment with a low dose of one or more AH peptides in a subject or patient in need thereof, and then increase the dosage, or systematically vary the dosage regimen, monitor the effects thereof on the patient or subject, and adjust the dosage or treatment regimen to maximize the desired therapeutic effect. Further discussion of optimization of dosage and treatment regimens can be found in Benet et al., in Goodman & Gilman's The Pharmacological Basis of Therapeutics, Ninth Edition, Hardman et al., Eds., McGraw-Hill, New York, (1996), Chapter 1, pp. 3-27, and L. A. Bauer, in Pharmacotherapy, A Pathophysiologic Approach, Fourth Edition, DiPiro et al., Eds., Appleton & Lange, Stamford, Conn., (1999), Chapter 3, pp. 21-43, and the references cited therein, to which the reader is referred.

The dosage levels and mode of administration will be dependent on a variety of factors such as the AH peptide(s) used, the context of use (e.g., the surface to be treated, the patient to be treated), and the like. Optimization of modes of administration, dosage levels, and adjustment of protocols, including monitoring systems to assess effectiveness are routine matters well within ordinary skill.

In addition, in certain embodiments, the AH peptides are delivered under conditions that enhance activity of the AH peptide in facilitating lysis of enveloped virus. For example, use of AH peptides can be under a temperature condition which enhances activity of the AH peptide in mediating lysis. For example, contacting the AH peptide with the material to be treated under a temperature 20° C. or greater, 25° C. or greater, or 30° C. or greater can provide for enhanced efficiency of viral lysis, e.g., so as to mediate lysis of at least 70%, at least 75%, at least 80%, at least 85% at least 90% or at least 95% of viral particles in a starting population. The temperature will generally be selected so as to be compatible with the use intended and/or the material to be treated (e.g., biological material versus non-biological material).

The pH conditions under which the AH peptide is delivered can also me modulated so as to enhance activity of the AH peptide in facilitating lysis of enveloped virus. For example a pH of 7.5 or less may be utilized, e.g., a pH of about 7.0, about 6.5, about 6.0, about 5.5, about 5.0, about 4.5, or about 4.0.

The concentration of one or more AH peptides can also be adjusted to facilitate efficient lysis of enveloped virus. For example, concentrations of about 1 µM, 2 µM, 3 µM, 4 µM, 5 µM, 6 µM, 7 µM, 8 µM, 9 µM, 10 µM, 11 µM, 12 µM, 13 µM, 14 µM, or 15 µM can be utilized. In some embodiments, an increase in the concentration of the AH peptide provides for an enhanced activity of the AH peptide in facilitating lysis of enveloped virus.

Where, the AH peptide is used in solution, the osmolality of the solution can be adjusted so as to facilitate efficient lysis of enveloped virus by the AH peptide. For example, the concentration of one or more salts in the solution can be adjusted such that an osmotic pressure equivalent to that of a solution with a NaCl concentration of about 100 mM, about 150 mM, about 200 mM, about 250 mM, about 300 mM, about 350 mM, about 400 mM, about 450 mM, about 500 mM, 550 mM, or about 600 mM is achieved.

Suitable conditions for use with the application of an AH peptide include those that provide for a microenvironment at the site of application that reflects one or more of these formulation parameters. It should be understood that benefit provided by the adjustment of one or more of the above parameters may depend on one or more of the other parameters. For example, as indicated in the Examples the benefit provided by adjusting pH or osmolality may depend on the concentration of AH peptide used in the formulation.

Exemplary methods are described below in further detail.

Disinfection and/or Sterilization Uses

The disclosure contemplates the use AH peptides in a variety of disinfection and/or sterilization methods.

For example, AH peptides find use in methods of reducing viral contamination from a biological material. "Biological materials" include, but are not limited to, biological fluids (e.g., blood), biological solutions comprising blood, a blood component, and cell culture or a component of a cell culture (with the proviso the enveloped virus to be treated with AH peptide is other than HCV).

Exemplary biological fluids include but are not limited to: whole blood; anti-coagulated whole blood (AWB); packed red cells obtained from AWB; platelet-rich plasma (PRP) obtained from AWB; platelet concentrate (PC) obtained from AWB or PRP; plasma obtained from AWB or PRP; red cells separated from plasma and resuspended in physiological fluid; and platelets separated from plasma and resuspended in physiological fluid. Blood product or biological fluid also includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate (PC), platelet-rich plasma (PRP, platelet-free plasma, platelet-poor plasma, plasma, or packed red cells (PRC); analogous blood products derived from blood or a blood component or derived from bone marrow. The biological fluid may include leucocytes, or may be treated to remove leucocytes. Each of these blood products or biological fluids may be processed in the manner described herein.

In general, the method comprises contacting the biological material with an AH peptide in an amount effective to provide for disruption of enveloped viral particles that may be present in the biological solution, where the AH peptides are present in an amount sufficient to disrupt enveloped virus in the blood which enveloped viruses are less than about 250 nm in diameter.

In one embodiment, the AH peptides are used in methods to provide for disinfection of whole blood and/or blood products. AH peptides can be used in the disinfection and/or sterilization of a variety of blood products such as whole blood for transfusion, blood cells, blood plasma and blood plasma proteins. Since whole blood is rarely used, the present methods are more particularly directed to processes for disinfecting compositions containing red blood cells and/or blood plasma. In certain embodiments, a method for treating blood and/or blood products involves contacting the blood and/or blood products with a composition comprising one or more AH peptides, where the AH peptides are present in an amount sufficient to disrupt enveloped virus in the blood which enveloped viruses are less than about 250 nm in diameter. The method may further include removing the AH peptides from the blood or blood product.

In another embodiment, biological materials, especially those which are flowable, can be treated with an AH peptide by contacting the biological solution with a surface having immobilized AH peptide. Thus the disclosure provides a substrate having an immobilized AH peptide on at least one surface such that In other embodiments, methods for disinfecting whole blood or blood products are provided which include the steps of providing a disinfectant composition of a disinfecting concentration of amphipathic α-helix (AH) polypeptides and a diluent, and then mixing whole blood or blood product with the disinfecting composition for a length of time sufficient to inactivate enveloped viruses having a diameter of less than about 250 nm that may be present in the blood or blood product. Mixing a disinfectant composition with blood or blood products can be performed by simply combining the blood or blood product and disinfectant composition in a suitable container with light agitation to assure sufficient interaction between the blood and disinfectant composition. Suitable containers include but are not limited to blood collection bags and blood storage apparatus. It may be desirable to use automated cell washing equipment known in the art. After the blood or blood product is disinfected, the AH peptide may be optionally separated from the treated composition, providing blood or blood product which is safe and effective for therapeutic use. Alternatively, it may be acceptable to maintain AH peptide in the treated blood. Such methods can be similarly applied for other flowable biological materials, such as plasma or plasma products, including plasma protein fractions.

The present disclosure also provides methods of disinfecting a material especially a flowable material, using a substrate having immobilized AH peptide. In this embodiment, AH peptides are immobilized on a substrate surface in a manner that maintains the ability of the AH peptide to disrupt a viral envelope. Exemplary methods include methods that provide for non-covalent or covalent immobilization to a substrate surface, where the substrate may be solid or semi-solid. Where the substrate is semi-solid and/or porous, the AH peptide may be immobilized on any solvent-accessible or air-accessible surface. Methods for immobilizing AH peptides can include coating, spraying, stamping, and the like. Covalent attachment to a surface can be accomplished by, for example, attachment of an AH peptide through a chemically modified amino acid which in turn can be attached to a substrate surface (e.g., a resin, bead, etc.). In some embodiments, the substrate is other than a cell culture dish or research reagent vial.

Flowable material which may contain an enveloped virus having a diameter of less than about 250 nm (e.g., is suspected or known to contain such a virus) is brought into contact with the immobilized AH peptides, e.g., by flowing the material over the surface and/or incubating the material with the AH peptide-containing surface.

In some embodiments, substrates having immobilized AH peptides are adapted for use in a biological fluid processing assembly. In general such substrates are constructed of any material compatible with a biological fluid, such as whole blood or a blood component, and where used in connection with a biological fluid processing assembly are further adapted to withstand centrifugation. Exemplary containers which may be adapted for use as AH peptide-immobilization substrates include blood collection and satellite bags (e.g., made from plasticized polyvinyl chloride, e.g. PVC plasticized with dioctylphthalate, diethylhexylphthalate, or trioctyltrimellitate). The bags may also be formed from polyolefin, polyurethane, polyester, and polycarbonate.

In one embodiment, the AH peptide-immobilization substrate is a lumen surface of a tubing, which may be any conduit or means which provides fluid communication between containers, such as containers for dispensing biological fluids. Further the AH peptide-immobilization substrates can include seals, valves, clamps, transfer leg closures, and the like which may be used in connection with delivery of blood or blood product to a subject.

A number of additional containers may be in communication with the biological fluid processing system, and can be utilized to define different flow paths. For example, an additional satellite bag containing physiological solution may be placed in communication with the biological fluid processing system.

AH peptides can also be used to provide for viral inactivation of tissues and organs used for transplantation. This can be accomplished by contacting the tissue or organ with an AH peptide (e.g., by perfusion with an AH peptide-containing solution) in an amount effective to reduce infection enveloped viruses that may be present in the tissue or organ, where the enveloped viruses are less than about 250 nm in diameter.

AH peptides can also be used similarly to antibacterial compositions (e.g., PURELL®, alcohol, and the like) to provide for disinfection of a biological or non-biological surface. Biological surfaces include skin (e.g., hands, site being prepped for surgery, etc.). In these contexts AH peptides can be administered in the form of formulated as topical creams, ointments, lotions, gels, powders, liquids, solids, detergents or soaps. Non-biological surfaces (e.g., countertops, medical instruments, and the like) can be treated with AH peptide-containing formulations, which can take the form of, for example, sprays, saturated towelettes, saturated sponges, and the like.

In some embodiments, methods for reducing viral contamination from medical devices, involve contacting the medical device with a composition containing one or more AH peptides, where the AH peptides are present in an amount sufficient to inactivate an enveloped virus where the AH peptides are present in an amount sufficient to disrupt enveloped virus that may be present in or on the medical device, where the enveloped viruses are less than about 250 nm in diameter. The method may further include removing AH peptides from the medical device. Examples of medical devices include those employed by a doctor, nurse, medical technician such as one who collects blood or blood products, or dentist (and as such "medical device" is meant to encompass "dental device").

The term "medical device" is intended to mean any tool employed in the checking, cleaning, and/or collection of fluid from or medical intervention of an animal or human body. Such tools include, without limitation, surgical instruments such as, but not limited to, probes, scalpels, clamps, forceps, needles, suction devices for removing saliva or blood including all nozzles, seals, tubing, filters, containers and reservoirs therein, endoscopes, optical fibers, transducers, wire, surgical loops, and in-line and out-line tubing and filters through which blood or blood product is passed prior to delivery to an individual and/or at the point of collection from an individual. Such medical devices can also serve as an AH peptide-immobilization substrate, as discussed above.

The disclosure also contemplate substrates that have been treated with an AH peptide, which substrates may have residual AH peptide, and may further have residual material resulting from disruption of viral envelopes. In one embodiment, the substrate is other than a cell culture dish or vial (e.g., such as used in a research laboratory setting). In some embodiments the material has a surface that contains immobilized AH peptide, as discussed above.

Also contemplated, are methods for reducing viral contamination of water or water containers such as found in swimming pools, hot-tubs, Jacuzzis, baths, and whirlpool baths, air-conditioners and humidifiers, involving contacting the water or water container with a composition with an AH peptide, where the AH peptides are present in an amount sufficient to disrupt enveloped virus that may be present, where the enveloped viruses are less than about 250 nm in diameter. Such water and water containers can be those found in the home, a hotel, spa or resort, office, or storage building.

It should be noted that in all embodiments of disinfecting methods using the AH peptides, the methods may be used for disrupting envelopes of an enveloped virus other than HCV.

The disinfecting AH peptide-containing compositions may include one or more additional compounds, as desired, with the proviso these additional compound do not significantly adversely affect activity of the AH peptide in disrupting viral envelopes of viruses of less than about 250 nm in diameter. For example, such compounds may be antimicrobial (e.g., antibacterial, antifungal) agents so as to enhance disinfection with respect to microorganisms.

Sufficient periods of time for accomplishing disinfection using the AH peptides as disclosed herein are primarily dependent upon the choice of AH peptide and the material to be disinfected. It can also be appreciated that useful AH peptide concentrations and periods of time for disinfecting are interdependent. AH peptide-containing compositions include those that are not suitable for administration to a subject, e.g., to a human subject. The phrase "not pharmaceutically acceptable" is meant to refer to a AH peptide-containing composition that contains, or contains at unacceptably high concentrations for pharmaceutical use, one or more compounds or solvents that are not suitable for administration to a subject by any route to effect an antiviral therapy. Examples of such components include a surfactant (e.g., detergent), preservative, solvent (e.g., DMSO) disinfectant, compound that provide for a scent, or other compound that is not suitable for administration to a subject, e.g., a human, by any route, e.g., by a parenteral route.

Use of AH peptides in the context of disinfection and/or sterilization can be carried out under conditions that provide for enhanced activity of the AH peptide in mediating viral lysis as discussed above. For example, contacting the AH peptide with the material to be treated under a temperature 20° C. or greater, 25° C. or greater, or 30° C. or greater can provide for enhanced efficiency of viral lysis, e.g., so as to mediate lysis of at least 70%, at least 75%, at least 80%, at least 85% at least 90% or at least 95% of viral particles in a starting population.

The suitable temperature used will be selected so as to be compatible with the materials to be disinfected/sterilized. For example, where the material is a biological material, such as blood or component thereof, the blood or component thereof can be contacted with the AH peptide under a temperature of 20° C. or greater, 25° C. or greater, or 30° C. or greater. pH and osmolality can also be adjusted as discussed previously herein provided that these conditions are consistent with maintaining the viability of the material to be disinfected/sterilized. In addition, the concentration of one or more AH peptides can also be adjusted to facilitate efficient lysis of enveloped virus in the context of disinfectant/sterilization uses. For example, concentrations of about 1 µM, 2 µM, 3 µM, 4 µM, 5 µM, 6 µM, 7 µM, 8 µM, 9 µM, 10 µM, 11 µM, 12 µM, 13 µM, 14 µM, or 15 µM can be utilized. In some embodiments, an increase in the concentration of the AH peptide provides for an enhanced activity of the AH peptide in facilitating lysis of enveloped virus.

Use in Antiviral Therapy

AH peptides can be used in antiviral therapy methods to treat any subject having, suspected of having, or susceptible to infection by an enveloped virus, especially an enveloped virus having an average particle diameter of less than 250 nm or less than 110 nm. Such subjects include human and non-human subjects, including without limitation, livestock (e.g., cattle, pigs, horses, sheep, etc.), poultry (e.g., chickens, turkeys, ducks, etc.), domestic pets (e.g., dogs, cats, etc.), and zoo animals. A precise diagnosis of the viral infection need not be necessary for use of the AH peptides. Instead, the clinician need only suspect that the viral infection be one that is enveloped and having a viral particle diameter susceptible to disruption by the AH peptide to be administered. Where desired, such a diagnosis can be made based on, for example, clinical signs and symptoms, diagnostic assay, and the like. In some embodiments, the viral infection to be treated is other than an HCV viral infection.

A variety of methods for administering antiviral agents are known and include, without limitation, parenteral administration (e.g., injection), aerosol administration, suppository, and, with proper design, oral administration.

Therapeutic compositions may include more than one AH peptide. The precise formulations and modes of administration of the AH peptide antiviral compositions will depend on the nature of the antiviral agent, the condition of the subject, and the judgment of the practitioner. Design of such administration and formulation is routine optimization generally carried out without difficulty by the practitioner.

In addition to the AH peptides, combination therapies including other antiviral agents can be administered in conjunction with AH peptides as disclosed herein. For example, it may be desirable to administer an AH peptide in combination with an agent such as interferon.

As discussed previously herein, AH peptide formulation parameters can be varied to provide for enhanced activity of the AH peptide in mediating viral lysis.

Conditions can be varied to suit the particular route of administration. For example, where an AH peptide is to be used in a topical formulation, it may be desirable to administer the AH peptide in a formulation having a pH of 7.5 or less. For example a pH of 7.5 or less may be utilized, e.g., a pH of about 7.0, about 6.5, about 6.0, about 5.5, about 5.0, about 4.5, or about 4.0. In addition, where an AH peptide is to be used in a topical formulation it may be desirable to adjust the concentration of one or more salts in the formulation such that an osmotic pressure equivalent to that of a solution with a NaCl concentration of about 100 mM, about 150 mM, about 200 mM, about 250 mM, about 300 mM, about 350 mM, about 400 mM, about 450 mM, about 500 mM, 550 mM, or about 600 mM is achieved.

The concentration of one or more AH peptides can also be adjusted to facilitate efficient lysis of enveloped virus in the context of an antiviral therapy. For example, concentrations of about 1 µM, 2 µM, 3 µM, 4 µM, 5 µM, 6 µM, 7 µM, 8 µM, 9 µM, 10 µM, 11 µM, 12 µM, 13 µM, 14 µM, or 15 µM can be utilized. In some embodiments, an increase in the concentration of the AH peptide provides for an enhanced activity of the AH peptide in facilitating lysis of enveloped virus.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods

The Materials and Method described below were used in connection with Examples 1-4. Materials and Methods varying from those described below are discussed in the context of the specific examples.

Amphipathic α-Helical (AH) and Non-Amphipathic Non-Helical (NH) Peptides

The amphipathic α-helical (AH) and non-amphipathic non-helical (NH) peptides were synthesized by Anaspec Corporation (San Jose, Calif., USA). The NH peptide was designed so as to introduce three charged amino acids spaced at intervals along the predicted alpha-helix of AH such that no sustained hydrophobic patch remained. The sequences of AH and NH are H-Ser-Gly-Ser-Trp-Leu-Arg-Asp-Val-Trp-Asp-Trp-Ile-Cys-Thr-Val-Leu-Thr-Asp-Phe-Lys-Thr-Trp-Leu-Gln-Ser-Lys-Leu-Asp-Tyr-Lys-Asp-NH2 (SEQ ID NO: 89) and H-Ser-Gly-Ser-Trp-Leu-Arg-Asp-Asp-Trp-Asp-Trp-Glu-Cys-Thr-Val-Leu-Thr-Asp-Asp-Lys-Thr-Trp-Leu-Gln-Ser-Lys-Leu-Asp-Tyr-Lys-Asp-NH2 (SEQ ID NO: 90), respectively (the introduced charged amino acids are indicated in bold).

Small Unilamellar Vesicle Preparation

Small unilamellar vesicles of 1-palmitoyl-2-oleoyl-sn-glycero-3-phosphocholine (POPC) (Avanti Polar Lipids, Alabaster, USA) were prepared by the extrusion method. For QCM-D and AFM measurements, we have used Tris buffer: 10 mM Tris [pH 7.5], 150 mM NaCl solution with 1 mM EDTA in 18.2 MΩ-cm MilliQ water (MilliPore, Oregon, USA). Extruded unilamellar vesicles (referred to simply as vesicles) were prepared according to the protocol described in Johnson et al. (2002) *Biophys J.* 83:3371-3379. Vesicles were generally prepared at a nominal lipid concentration of ~5 mg/ml for QCM-D and AFM then subsequently diluted before experiments. Vesicles were generally used within one hour of preparation.

Dynamic Light Scattering

Dynamic light scattering (DLS) was performed by a 90Plus Particle Size Analyzer and results analyzed by a digital autocorrelator software (Brookhaven Instruments Corporation, New York, USA). All measurements were taken at a scattering angle of 90° where the reflection effect is minimized. All autocorrelation functions obtained were also analyzed by CONTIN and Non-Negatively Constrained Least Squares (NNLS) algorithms to check for multimodal distributions.

Quartz Crystal Microbalance-Dissipation (QCM-D)

A Q-Sense D300 (Q-Sense AB, Gothenburg, Sweden) equipped with a QAFC 301 axial flow chamber was used to conduct QCM-D measurements. AT-cut crystals (Q-Sense) of 14 mm in diameter with 50 nm thermally evaporated gold and $TiO_2$ were used for all vesicle interactions and adsorptions. The crystal was driven at its resonance frequency of 5 MHz, and the frequency and dissipation changes for the three overtones at 15, 25, and 35 MHz were also monitored. To capture the characteristic dissipation, the drive circuit was short-circuited and the exponential decay of the crystal oscillation was recorded. The temperature of the Q-Sense cell was set at 25.0° C. and accurately controlled by a Peltier element in the cell with fluctuation smaller than ±0.1° C. Each QCM crystal was treated with oxygen plasma at ~75 watts for ~5 minutes prior to measurements (March Plasmod Plasma Etcher, March Instruments, California, USA).

QCM-D Sensor

Quartz crystal microbalance-dissipation (QCM-D) devices were the first piezoelectric devices used in a detection application (Sauerbrey et al. (1959) *Z. Physik* 155: 206) and have played an important role in probing interfacial processes or acoustic properties of liquids. The operation of a QCM relies on the excitation into mechanical resonance induced by an electrical field across the quartz crystal with two metal electrodes on opposite sides of the quartz crystal plate. The acoustic waves generated in QCM devices are bulk transverse waves that travel in a direction perpendicular to the plate surfaces. Particle displacements at these surfaces are parallel to the surface (shear waves). The plate thickness d determines the wavelength λ of the fundamental (n=1) and harmonic (n=3, 5, . . . ) resonances according to λ=2d/n.

Therefore:

$$f_n = n \cdot f_0 = \frac{n \cdot v}{2d} \qquad (1)$$

where $f_0$, $f_n$ are the resonant frequencies of the fundamental mode (n=1) and the $n^{th}$ overtone (n=3, 5, . . . ), respectively, and v is the velocity of sound (v=3340 m/s in AT cut quartz).

The resonant frequency of the fundamental mode is typically between 5 and 20 MHz and increases as the plate thickness decreases. From these factors deduced a relationship for determining of mass changes in thin films at the sensor surface, $$\Delta f_s = -\frac{2 \cdot f_0 \cdot f_n}{\sqrt{\rho_q \cdot \mu_q}} \cdot \Delta m = -C_f \cdot \Delta m \qquad (2)$$

where $\Delta f_s$ is the change of the resonant frequency, $\rho_q$ is the density and $\mu_q$ is the shear modulus of the quartz crystal, respectively, $\Delta m$ is the mass per area and $C_f$ is the sensitivity constant. This relation is valid for thin, rigid films with a uniform mass distribution.

Due to this mass sensitivity a QCM sensor can be used for monitoring film thickness and mass deposition on the surface of a quartz crystal. With the same technique electrochemical or immunochemical mass deposition on a quartz crystal immersed in liquids can be detected (Aberl et al. (1994) *Sensors and Actuators B-Chemical* 18: 271-275; Andersson et al. (2003) *J. Biomed Mater Res A* 64: 622-629. Drost et al. (1998) *Trends and New Applications of Thin Films* 287-2: 521-524; Fetchko & Stagljar (2004) *Methods* 32: 349-362; Fredriksson et al. (1998) *J. Mater Sci Mater Med* 9: 785-788).

In the case of measurements in liquids, the additional effect of the acoustic properties of liquids on the sensor signal has to be considered. Kanazawa & Gordon, (1985) *Anal. Chim. Acta* 175: 99-106, derived a relationship that expresses the change in oscillation frequency of a quartz crystal in contact with a fluid, $$\Delta f_K = -f_0 \cdot f_n^{\frac{1}{2}} \cdot \sqrt{\frac{\rho_1 \cdot \eta_1}{\Pi \cdot \rho_q \cdot \mu_q}} \quad (3)$$

where $\Delta f_K$ is the change of the resonant frequency and $\rho_1$ and $\eta_1$ are the density and viscosity of the liquid in contact with the sensor surface, respectively.

Atomic Force Microscopy (AFM)

The AFM experiments were carried out on a XE-100 (PSIA Sungnam, Korea) in contact mode and non-contact mode. Rectangular-shaped $Si_3N_4$ cantilevers were used (ORC8C, Veeco, Santa Barbara, Calif.). The cantilevers had a force constant of k=0.05 N/m and average tip radius of 15 nm. All measurements were performed in a Tris buffer (150 mM NaCl, 10 mM Tris [pH 7.5], 1 mM EDTA) using an open liquid cell (PSIA Sungnam, Korea) with an injection tube. Images of vesicles were obtained both in the "contact" mode with an imaging force of less than 100 pN and with "non-contact" mode in fluid. However, images presented in this manuscript were only obtained in the "non-contact" mode in fluid. The scan line speed was optimized between 0.3 Hz to 2 Hz with a pixel number of 256×256, depending on the scan size. Images were recorded in height, amplitude, phase, and error modes. All measurements were done on the height images. All images shown were subjected to a first order plane-fitting procedure to compensate for sample tilt. The cross-sectional analysis was carried out on images subjected only to a first order plane-fitting procedure. Topographical and grain analyses of lipid vesicles and bilayers were performed using the software XEI 1.5 supplied by PSIA (Sungnam, Korea).

Example 1

AH Peptides Ruptures Vesicles

The ability of an amphipathic α-helix (AH) peptide to disrupt vesicles was demonstrated using an AH peptide derived from the N-terminus of the hepatitis C virus NS5A protein (Elezar et al. 2003 *J. Virol* 77:6055-61). AH and NS peptides were produced by standard chemical synthetic methods. FIG. 1, Panels a-c provide schematic representations of the amphipathic alpha helix (AH) peptide (FIG. 1, Panel a) and a non-amphipathic, non-helical (NH) peptide (FIG. 1, Panel b), as well as a schematic illustrating creation of a bilayer on Au and on $TiO_2$ surfaces (FIG. 1, panel c).

The left side of FIG. 1, Panel a shows a space-filling model of the AH peptide, which is derived from the first 31 amino acids of the hepatitis C virus (HCV) nonstructural protein NS5A's N-terminal alpha helix. The sequence of this AH peptide is SGSWLRDVWDWICTVLTDFK-TWLQSKLDYKD (SEQ ID NO: 89). Hydrophobic and hydrophilic amino acids are shaded in white and grey, respectively. The arrow indicates a 90 degree rotation about the y-axis, which leads to the image on the right side of FIG. 1, Panel a. The black/red circle around the AH illustrates the amphipathicity of this peptide.

FIG. 1, Panel b provides an analogous depiction of the NH peptide that differs from AH by the substitution of charged amino acids for hydrophobic ones at three positions. The sequence of NH is SGSWLRDDWDWECTVLTD DKTWLQSKLDYKD (SEQ ID NO: 90) (where the three point mutations are indicated in bold and underlined). These substitutions were spaced at intervals along the predicted α-helix such that no sustained hydrophobic face remained. Circular dichroism measurements indicate that the helical structure of AH is disrupted by the mutations in NH. Moreover, the amphipathic nature of the peptide is disrupted, as illustrated in FIG. 1, Panel b, right side.

The top left of FIG. 1, Panel c is a macroscopic idealization of vesicle adsorption on a gold quartz crystal. Zooming in, only the outer leaflet of a vesicle is illustrated. When the vesicle is exposed to AH peptides, the latter are speculated to first bind onto the outer leaflet and then open up the vesicle, as shown, exposing the inner leaflet to the solvent. It is hypothesized that AH peptides induce pores, which then drive the disruption of the vesicle, which is accompanied in this system by the formation of bilayers. The result is a bilayer devoid of all vesicles. Note, for purposes of illustration, the bilayer is scaled down to the size of vesicles, which is why the substrates appear larger.

In order to systematically investigate the ability of AH peptides to rupture vesicles, synthetic vesicles were initially tested. The vesicles were made by extrusion through 30 nm polycarbonate etch-tracked (PEC) membranes on a gold surface in the absence of the AH peptide, the peptide was then introduced to induce bilayer formation. It has been well documented that the high polarizability of the gold surface maximizes the attractive potential, which is the driving force that enables vesicles to remain intact and stable on a gold support (Keller & Kasemo (1998) *Biophys J.* 75: 1397-1402; Keller et al. (2000) *Phys Rev Lett* 84: 5443-5446; Reimhult et al. (2002) *Phys. Rev. E* 66 (5 Pt 1), 051905; and Reimhult et al. (2003) *Langmuir* 19: 1681-1691).

When vesicles adsorb, a large amount of trapped water exists within the intact vesicles as well as between vesicles adsorbed on the surface. This trapped water is able to dissipate a large amount of energy (FIG. 2, Panel 2-1, sub-panel a), unlike the water that rests on top of a bilayer. Due to the viscoelastic nature of the films, the large energy dissipation ($\Delta D \sim 8 \times 10^{-6}$) leads to an underestimation of the layer thickness using the Sauerbrey equation (Voinova et al. (2004) *Spectroscopy-an International Journal* 18: 537-544). This underestimate can be corrected by applying the viscoelastic model described by Voinova et al. (Voinova et al. (2004) *Spectroscopy-an International Journal* 18: 537-544; Voinova et al. (2002) *Biosensors & Bioelectronics* 17: 835-841; Voinova et al. (1999) *Physica Scripta* 59, 391-396). After introducing 0.05 mg·ml$^{-1}$ of the AH peptide to the vesicle layer on the gold surface (FIG. 2, Panel 2-1, sub-panel b), a large frequency decrease (~40 Hz) as well as a dissipation increase (about 14×10$^{-6}$) occur within two minutes. This result, although unexpected, provides a clue in our effort to understand the molecular interactions that occur when the AH peptide and lipid bilayer interact.

One possible explanation for this phenomenon is that the AH peptide first creates an instability on the vesicle surface by electrostatic interaction. This may lead to expansion of the vesicles (Gidalevitz et al. (2003) *Proc Natl Acad Sci* USA 100: 6302-6307) as well as to the creation of microvilli (Mecke et al. (2005) *Biophys J.* 89, 4043-4050; and Sato et al. (1996) *Biochim Biophys Acta* 1285:14-20) (finger-like structures) on the outer leaflet of the vesicles (Bellomio et al. (2005) *J Colloid Interface Sci* 285: 118-124). This could explain both the large changes in frequency due to the presumed expansion of vesicles as well as the increase in dissipation ascribable to both expansion and microvilli structure. The most exciting results are that the final frequency shift relative to the initial state was 25.5 Hz±0.5, and the final dissipation value was only 0.08×10$^{-6}$ (FIG. 2, Panel 2-1, sub-panel (b)), both values corresponding to a complete bilayer. According to the Sauerbrey equation, from which the bilayer thickness can be calculated, these QCM-D parameters indicate a transition of the vesicles to a thin and rigid bilayer film as a result of the action of the AH peptide.

Figures 1, 2:
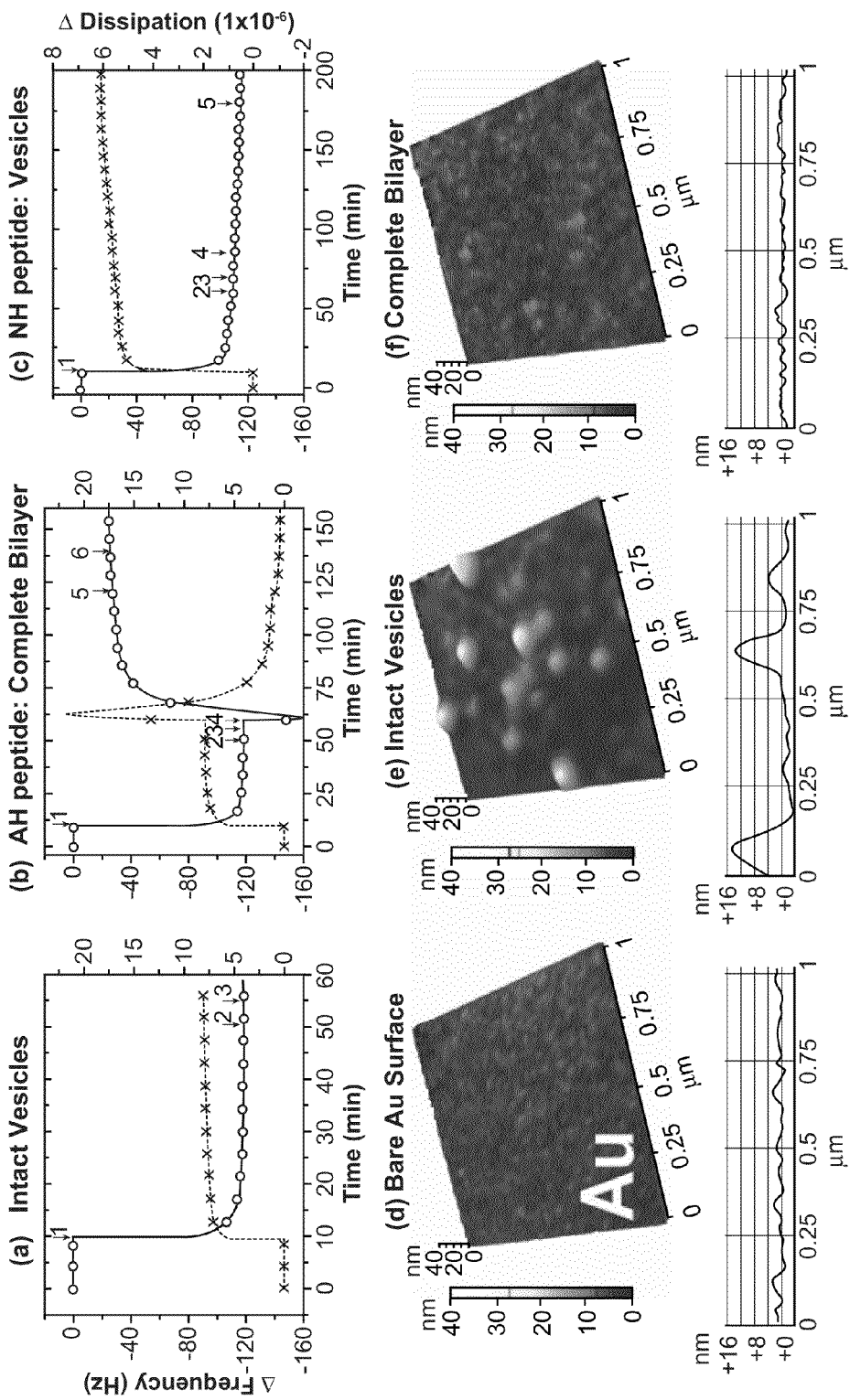
FIG. 2 provides the results of an analysis of the rupturing and fusion process of bilayer formation from vesicles on Au (Panel 2-1) and TiO2 (Panel 2-2) by QCM-D and AFM. Panel 2-1, sub-panels a-c, show the change in QCM resonant frequency and dissipation as a function of time for novel bilayer formation process on gold surface. (Sub-panel a) Δf(t) (blue curve) and ΔD(t) (red curve) show vesicle adsorption on oxidized gold surface. After 10 min (arrow 1) of stabilizing frequency signal, POPC vesicle solution was injected into the liquid cell. After 50 and 55 min (arrows 2 and 3), the same buffer was used for two washes. (Sub-panel b) At 60 min (arrow 4), the amphipathic α-helix peptide (AH peptide) solution was added (0.05 mg/ml) to the intact vesicles on the gold surface. After 120 and 140 min (arrows 5 and 6), the same buffer was used for two washes and the stability of the bilayers on the gold surface was observed. (Sub-panel c) The effect of the NH peptide was studied in an analogous manner to the AH peptide as described for FIG. 2, panel 2-1, sub-panel (b). Panel 2-1, sub-panels d-f, show AFM images demonstrating intact vesicles rupturing and spreading after addition of AH peptide on Au surface. The images are presented in the Height mode. (Sub-panel d) Bare Au surface. (Sub-panel e) Vesicles (0.1 mg/ml) deposited on Au surface. (Sub-panel f) After treatment with the AH peptide (0.05 mg/ml).
Figure 2:
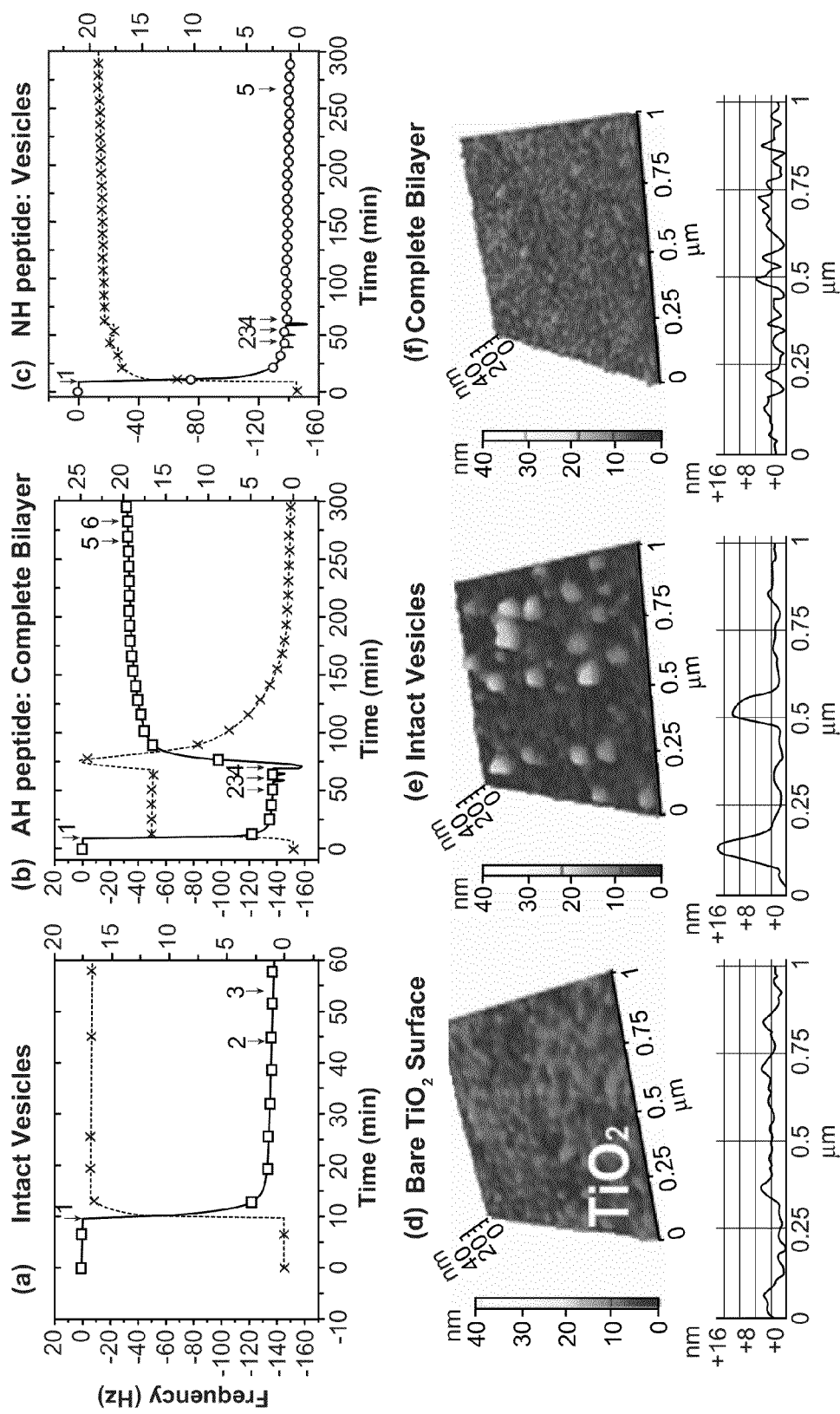
Figure 3:
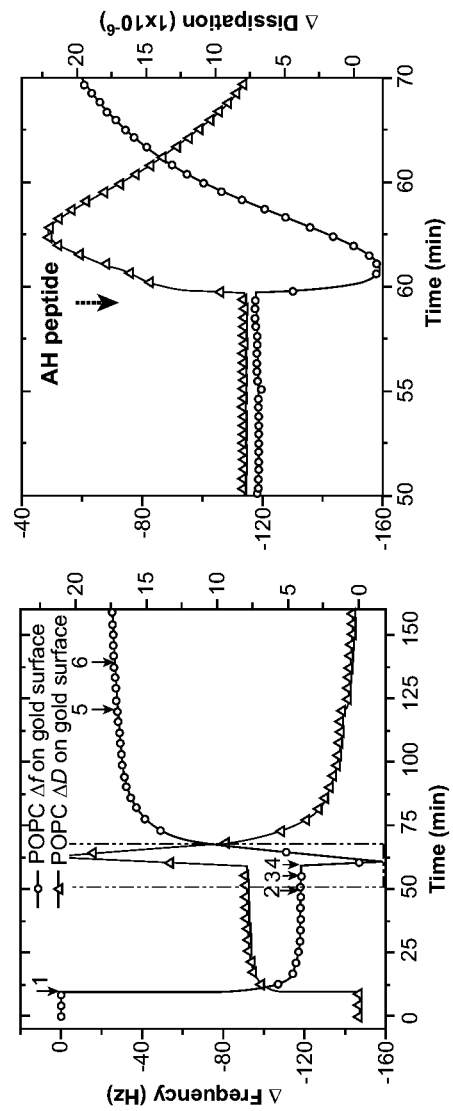
FIG. 3 shows a reprint and magnification of the AH binding kinetics of FIG. 2, panel 2-1, sub-panel (b). The blue highlighted portion on the left panel is enlarged to demonstrate binding of AH peptide on the adsorbed vesicle layer. The high frequency change is due to expansion of the vesicles (~30% change in mass), which is followed by AH peptide-induced vesicle destabilization and rupture, with resulting loss of lipid mass upon bilayer formation. The corresponding high energy dissipation change is due to expansion of vesicles as well as the formation of finger-like microvilli structures.

To further verify that the AH peptide, with its amphipathic α-helical structure, destabilized the vesicles, we repeated the experiments under the same conditions using a modified peptide in which three charged amino acids were introduced into the hydrophobic face of the AH peptide (Elazar et al. (2003) *J. Virol.* 77:6055-6061), disrupting its amphipathic nature and destroying its helical structure. As shown in FIG. 2, Panel 2-1, sub-panel (c), this non-helical peptide (termed NH peptide) does not destabilize intact vesicles since there are no changes in Δf and ΔD after injection of the NH peptide. This indicates that the amphipathic helical structure is one of the essential characteristics in vesicle destabilization.

While the QCM-D results demonstrate the process of kinetic changes from adsorption of vesicles to the formation of bilayers, we utilized atomic force microscopy (AFM) in order to confirm and directly display rupture of vesicles and bilayer formation by the destabilizing agent, the AH peptide. AFM examined the bare Au surface as a control with Rq of 1.13±0.21 nm (±S.E. n=8). Vesicles (0.1 mg/ml) were carefully added through the injection system, incubated for 30 minutes, and thoroughly rinsed three times with Tris buffer. Intact vesicles were clearly identified by AFM and the average Rq increased to 2.49±0.32 nm (±S.E. n=8), as shown in FIG. 2, panel 2-1, sub-panel (e).

The AFM images in FIG. 2, panel 2-1, sub-panel (f) show the effect of the AH peptide on the vesicles as a destabilizing agent, which we examined by injecting the peptide (0.05 mg/ml) and incubating the solution for 2 hours prior to scanning the images. These images clearly confirm the QCM-D data, indicating that vesicles ruptured as a result of the treatment with AH peptide. The average Rq of 1.67±0.12 nm (±S.E. n=15) indicated that the roughness became similar to the bare Au surface (average Rq of 1.32±0.25 nm (±S.E. n=8)), as expected for a bilayer. Grain analysis identified no vesicle-like structures (P≤0.001), indicating that the AH peptides ruptured vesicles to form bilayers. These results correlate with the QCM-D kinetic data shown in FIG. 2, Panel 2-1, sub-panel (b). An identical experiment has been done on TiO$_2$ (FIG. 2, Panel 2-2) and has shown similar results.

This example thus demonstrates that an AH peptide destabilizes and ruptures the leaflets of intact lipid vesicles. In addition, the ruptured vesicles to fuse and form planar bilayers on preferred solid substrates, such as gold and TiO$_2$.

Example 2

Interaction Between AH Peptides and Different Size Vesicles

In general, formation of a bilayer through vesicle rupture depends on two major factors—vesicle-surface interaction and vesicle-vesicle interaction. For both these interactions, the outcome (intact vesicles or bilayers) depends on the elastic properties and cohesive strength of the vesicles themselves (Reimhult et al. (2003) *Langmuir* 19 (5): 1681-1691; Reimhult et al. (2002) *Journal of Chemical Physics* 117 (16): 7401-7404; Reimhult et al. (2002) *Phys Rev E Stat Nonlin Soft Matter Phys* 66, (5 Pt 1), 051905; Keller & Kasemo (1998) *Biophys J* 75 (3): 1397-1402; and Keller et al. (2002) *Phys Rev Lett* 84 (23): 5443-6).

Figure 4:
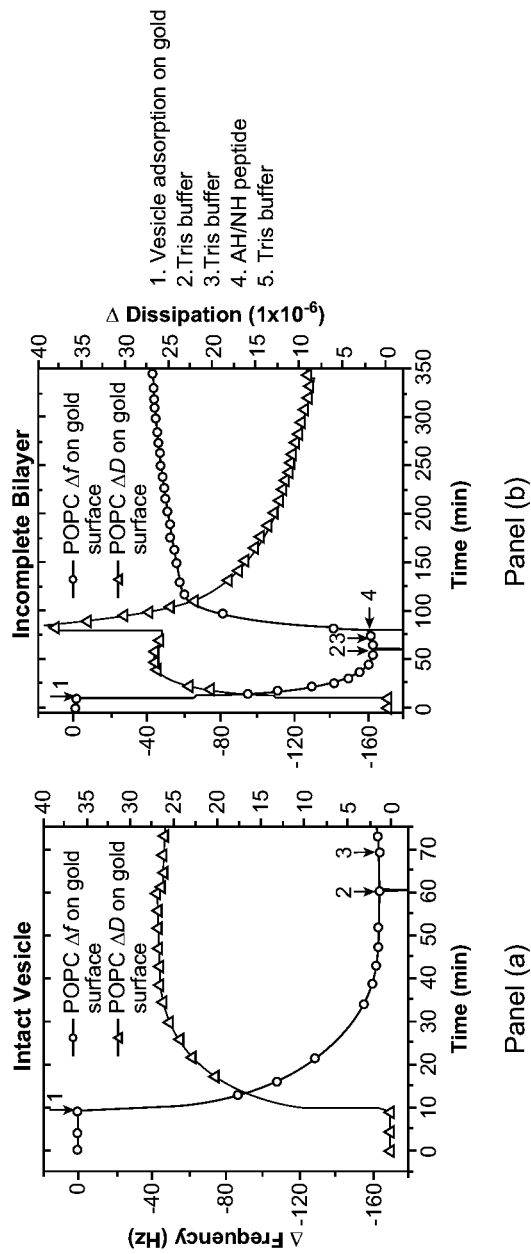
FIG. 4: Change in QCM resonant frequency and dissipation as a function of time for novel bilayer formation process on gold surface (Ø100 nm PEC=148 nm±1.4 nm) Panel (a): In order to study the rupturing strength of the AH peptide, a similar test as in FIG. 2, Panel 2-1, sub-panel (a), using larger vesicles (Ø100 nm PEC=148 nm±1.4 nm) was performed. After 10 min (arrow 1) of stabilizing the frequency signal, the POPC vesicle solution (0.1 mg/ml) was injected into the liquid cell. After 60 and 70 min (arrows 2 and 3), the same buffer was used for two washes and the stability of the intact vesicles on the gold surface was observed. Panel (b): At 80 min (arrow 4), the amphipathic α-helix peptide (AH peptide) solution was added (0.05 mg/ml) to the intact vesicles (Ø100 nm PEC=148 nm±1.4 nm) on the gold surface. The peptide destabilized and ruptured the vesicles, but did not make a complete bilayer. After 340 min (arrow 5), two buffer washes were performed and the stability of the bilayers on the gold surface was observed.

In order to test the limitation of the rupturing strength of the AH peptide, the formation of bilayers on gold surfaces from vesicles of different sizes was studied. Larger vesicles (Ø=148 nm±1.4 nm) were first injected onto a gold surface (as in FIG. 4, Panel a), and then the AH peptide was applied (FIG. 4, panel b). However, under these conditions the AH peptide did not provide for complete rupture of vesicles extruded through 100 nm PEC membranes, which provides for production of vesicles having an average diameter of about 148 nm. This is presumably as a result of the significant difference in the radii of the curvature of the vesicles extruded through 100 nm PEC (about 75% of vesicles rupture) versus 30 nm PEC, the latter of which have an average diameter of about 58 nm (approximately 100% of vesicle ruptured). The lack of formation of a complete bilayer is evidenced by a decrease of the final frequency by 50 Hz±2.5 (compared to 25 Hz for a complete bilayer) and a maximum decrease of the dissipation shift to only 9×10$^{-6}$ (compared to 0.08×10$^{-6}$ for a complete bilayer) as shown in FIG. 4, panel (b). During the rupturing process, vesicles must possess a high line-tension in order for peptides to trigger destabilization and rupture of the vesicles, thus forming complete planar bilayers.

These results suggest that the efficiency of AH peptides in rupturing vesicles decreases with increasing vesicle size. There may be a target size limit to the vesicle-destabilizing effect of the AH peptide related to the increased line tension associated with smaller diameter vesicles, which becomes less prominent as a function of increasing vesicle diameter. Based on the detergent binding properties of the amphipathic α-helical peptide, the location of its amino acids, and the findings of an NMR study (Penin et al. *J Biol Chem* (2004), and without being held to any particular theory, it is proposed that the mechanism of penetration into its target membrane is via the hydrophobic face of the helix within the cytoplasmic leaflet of the membranes.

Example 3

Detailed Description Regarding Bilayer Formation on a TiO$_2$ Surface

In order to prove that vesicle rupture is triggered by the AH peptide and is surface independent, TiO$_2$ surfaces, which are known to have higher polarizability and a higher isoelectric point than SiO$_2$ (pH5.5 vs. pH2.3) (Kataoka et al. (2004) *Langmuir* 20: 1662-1666), were used. This provides compatible circumstances for the system, as these characteristics cause a low density of surface charges on TiO$_2$, and lead to intact vesicle deposition on TiO$_2$ surfaces. Similar experiments were performed on a TiO$_2$ surface to those previously performed on the Au surfaces, as shown in FIG. 5, Panels a-e.

Figure 5:
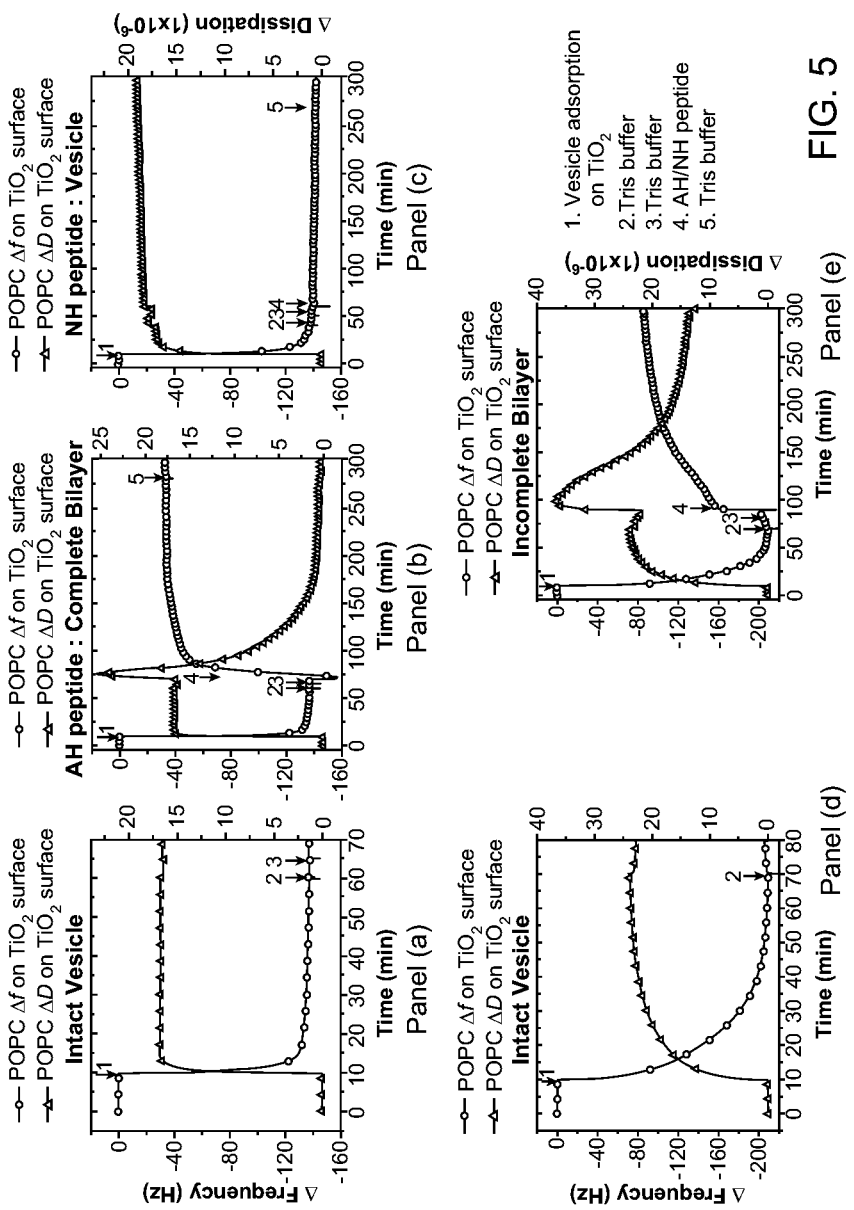
FIG. 5, Panels (a-e): Change in QCM resonant frequency and dissipation as a function of time for novel bilayer formation process on $TiO_2$ surface. (Ø30 nm PEC=59 nm±0.2 nm, Ø100 nm PEC=148 nm±1.4 nm) (Panel a) Δf(t) (blue curve) and ΔD(t) (red curve) show vesicle adsorption on a $TiO_2$ surface. After 10 min (first arrow) of stabilizing the frequency signal, the POPC vesicle solution (Ø30 nm PEC) was applied to the liquid cell. After 60 min (second arrow), two buffer washes were performed and the stability of the intact vesicles on the $TiO_2$ surface was observed. (Panel b) After 55 min (arrow 4), the amphipathic α-helical AH peptide solution was added (0.05 mg/ml) to the intact vesicles (Ø30 nm PEC) on the $TiO_2$ surface. The AH peptide destabilized and ruptured the vesicles, making a complete bilayer. In (Panel c), the effect of the NH peptide was examined in a similar manner to that done with the AH peptide in Panel b. After 10 min (arrow 1) of stabilizing the frequency signal, the POPC vesicle solution (Ø30 nm PEC) was applied to the liquid cell. After 40 and 50 min (arrows 2 and 3), two washes with the same buffer were performed and the stability of the intact vesicles on the $TiO_2$ surface was observed. At 60 min (arrow 4), the non-amphipathic α-helix peptide (NH peptide) solution was added (0.05 mg/ml) to the intact vesicles on the $TiO_2$ surface. The NH peptide does not show any evidence of destabilizing and rupturing the vesicles. After 270 min (arrow 5), two buffer washes were performed and the stability of the intact vesicle bilayers on the $TiO_2$ surface was observed. (Panel d): In order to study the rupturing strength of the AH peptide, we performed a similar test as in FIG. 2, panel 2-2, (sub-panel b), but added a larger size POPC vesicle solution (Ø100 nm PEC) to the $TiO_2$ surface. (Panel e): After 60 min (arrow 4), the amphipathic α-helix peptide (AH peptide) solution was added (0.05 mg/ml) to the intact vesicles on the $TiO_2$ surface. The peptide destabilized and ruptured the vesicles, but did not make a complete bilayer.

As hypothesized, vesicle rupture induced by the AH peptide leads to the formation of complete bilayers (see FIG. 5, Panel b). In addition, it is clearly demonstrated that in the case of larger vesicles extruded through the 100 nm PEC, the AH peptide did not completely rupture all the vesicles similar to what was observed on a gold surface (see FIG. 5, Panel e).

Example 4

Effect of AH Peptide on 148 Nm±1.4 Nm POPC Vesicles on a TiO$_2$ Surface

Figure 6:
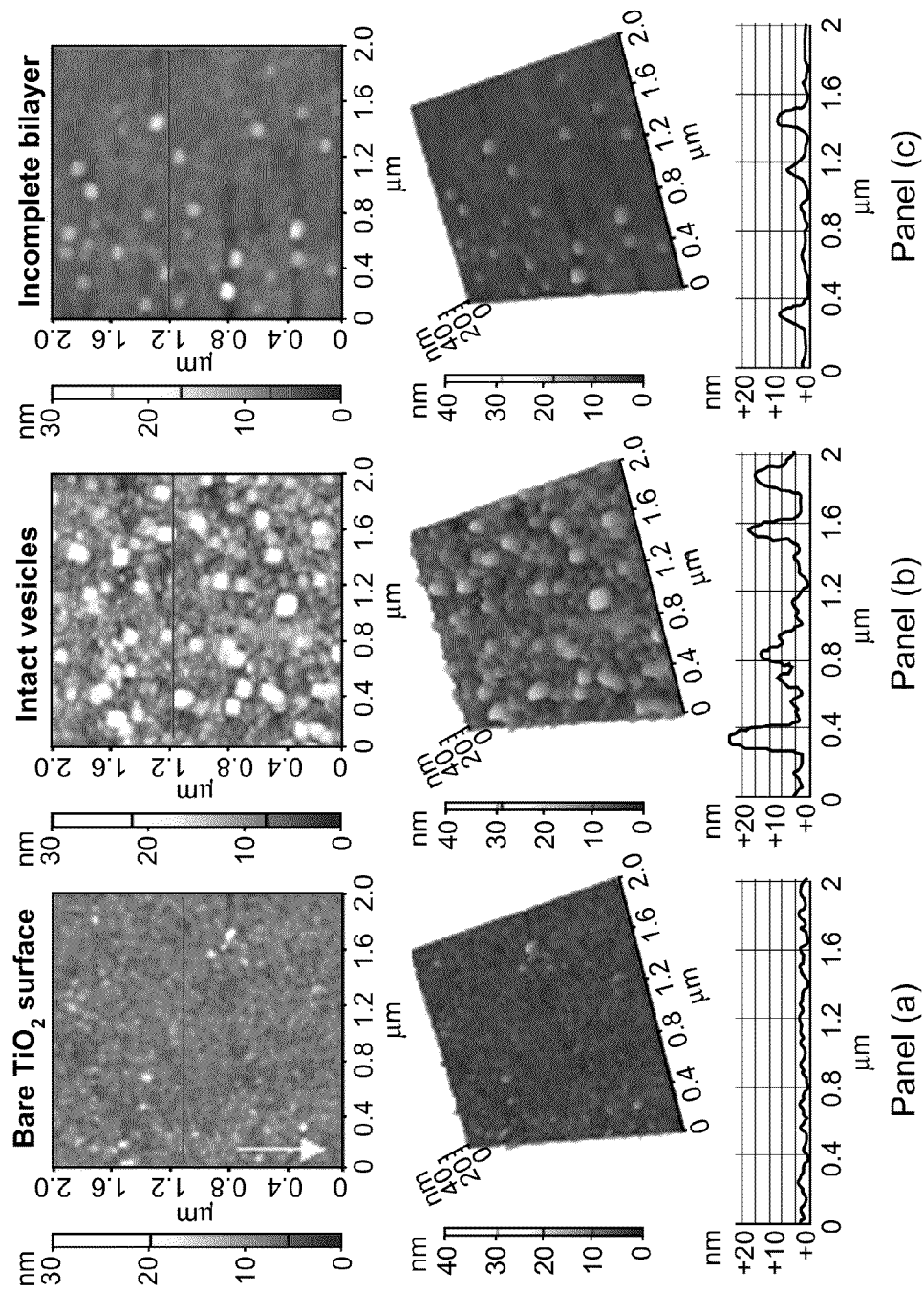
FIG. 6, Panels (a-c) show AFM images demonstrating intact vesicles rupturing and spreading after addition of AH α-helical peptide on a $TiO_2$ surface. The images, collected in buffer (150 mM NaCl, 10 mM Tris [pH 7.5], 1 mM EDTA), are presented in the height mode. All scan sizes are 2×2 μm and the arrows along the side of the frames in FIG. 6, panel a, indicate the slow scan direction. (Panel a): Bare $TiO_2$ surface. (Panel b): Vesicles (0.1 mg/ml) deposited on $TiO_2$ surface. (Panel c): After treatment with AH peptide (0.05 mg/ml), the AFM image demonstrated that some vesicles form a bilayer as a result of treatment of AH Peptide after 120 min. However, vesicles were not ruptured completely within 3 hours. Only 100 to 200 nm hyperbola-shaped objects were counted as vesicles.
Figure 7:
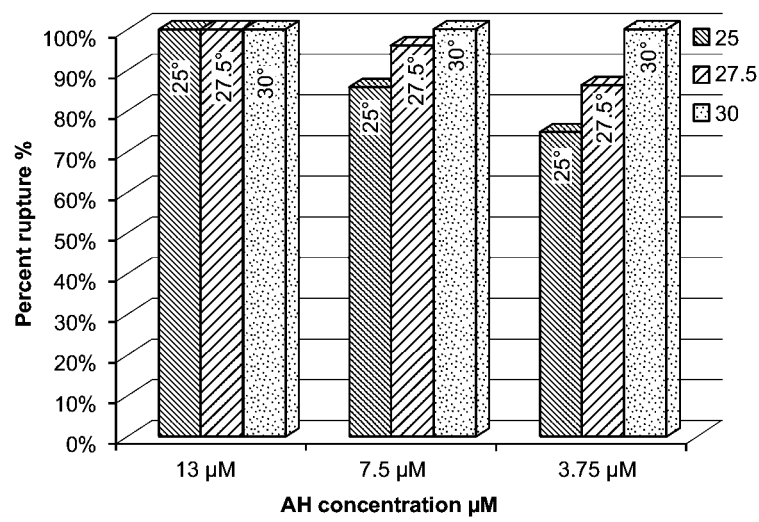
FIG. 7 provides a graph which shows the effect of increased temperature on the efficiency of AH peptide mediated vesicle lysis.
Figure 8:
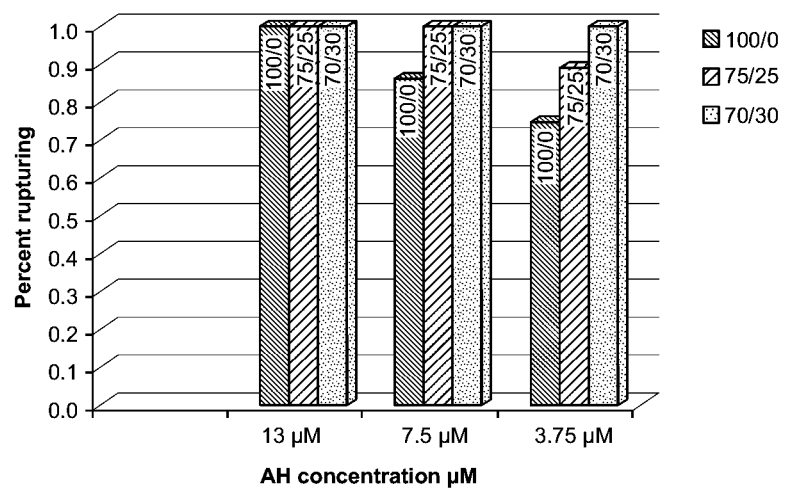
FIG. 8 provides a graph which shows the effect of altering the lipid composition of vesicles on the efficiency of AH peptide mediated vesicle lysis.
Figure 9:
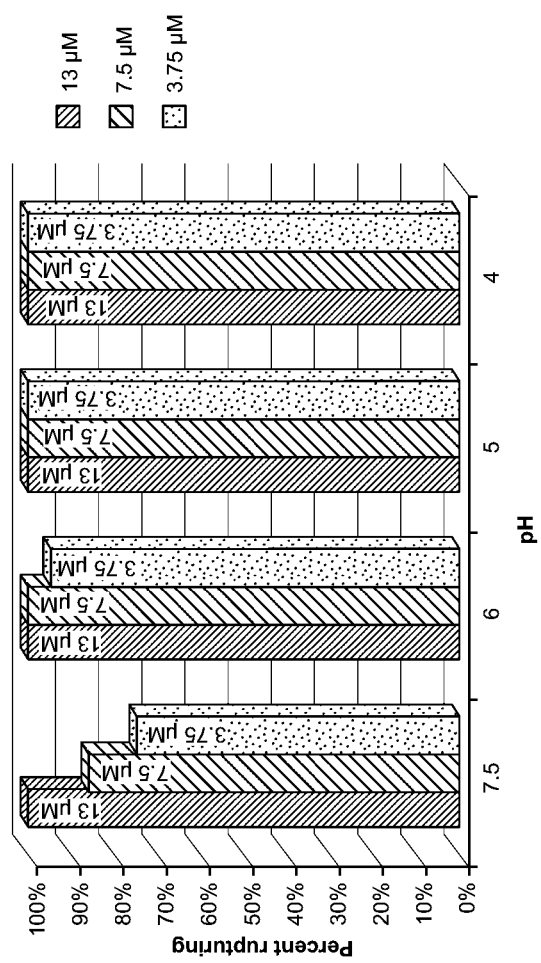
FIG. 9 provides a graph which shows the effect of decreased pH on the efficiency of AH peptide mediated vesicle lysis.
Figure 10:
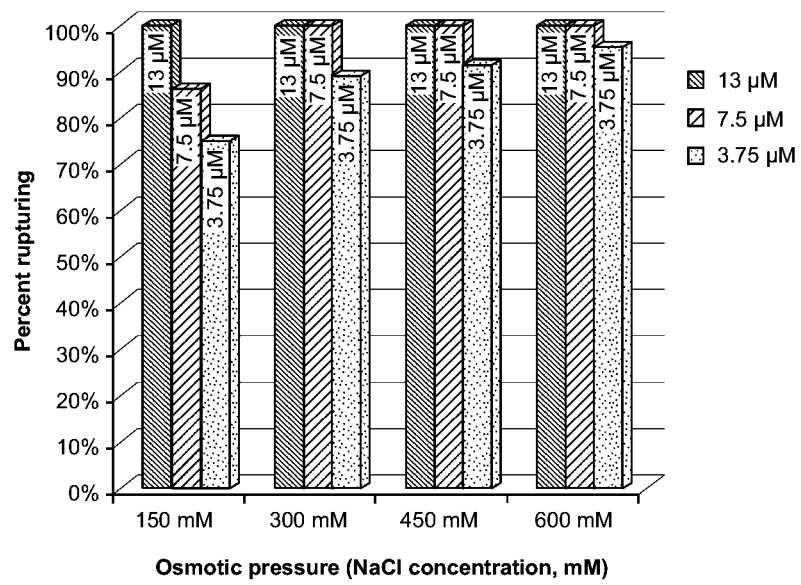
FIG. 10 provides a graph which shows the effect of increased osmotic pressure between leaflets of vesicles on the efficiency of AH peptide mediated vesicle lysis.

In a parallel experiment to that with QCM-D, AFM was used to test the ability of larger vesicles to fuse on a TiO$_2$ surface. FIG. 6, Panel b, demonstrates the vesicles extruded through 100 nm PEC membranes and deposited on the TiO$_2$ surface, which had an average Rq of 3.889 nm. Grain analysis identified 21 vesicles with an average diameter of 132.75±5.55 nm (±S.E. n=21). The cross section of the area identified by the red line (measured from height images) shows the height of the vesicles to be approximately 20 nm. The AFM images indicate that vesicles ruptured as a result of treatment with the AH peptide at 0.05 mg/ml concentration, as shown in FIG. 6, Panels b and c. The average Rq became 1.347 nm and the grain analysis identified 13 vesicles with an average diameter of 121.13±5.28 nm (±S.E. n=5), which correlates with the QCM-D data.

Example 5

Effect of Lysis Conditions on Efficiency of AH Peptide Mediated Lysis of Vesicles In order to determine the effect of various conditions on the efficiency of AH peptide mediated lysis of vesicles, AH peptides were contacted to vesicles while varying the following parameters: temperature, lipid composition of vesicles, pH and osmotic pressure between leaflets of vesicles. Three concentrations of AH peptide (13 μM, 7.5 μM and 3.75 μM) were tested for their ability to rupture vesicles having an average diameter of 75 nm while varying one of temperature, lipid composition of vesicles, pH and osmotic pressure between leaflets of vesicles from a standard set of conditions which included Tris buffer with NaCl at 150 mM, a temperature of 25 deg. C., a pH of 7.5 and a vesicle composition of PC/PS=100/0. The PC/PS ratio refers to the weight percentage of POPC (1-Palmitoyl-2-Oleoyl-sn-Glycero-3-Phosphocholine) relative to the weight percentage of DOPS (1,2-Dioleoyl-sn-Glycero-3-Phosphoserine) used in the preparation of the vesicles.

The results of the above experiments are shown in FIGS. 7-10 and summarized in Table 1 below (%=% of vesicles ruptured as calculated using linear Sauerbrey model or equation described previously herein). Data is based on measurements made using a Q-Sense E-4, multiple channel system (Q-Sense AB, Gothenburg, Sweden).

Vesicles were prepared such that the inner compartment of the vesicle contained approximately 150 mM NaCl.

TABLE 1

|  | 13 μM | 7.5 μM | 3.75 μM |
|---|---|---|---|
| Temperature |  |  |  |
| 25 | 100% | 86% | 75% |
| 27.5 | 100% | 96% | 86% |
| 30 | 100% | 100% | 100% |

TABLE 1-continued

|  | 13 μM | 7.5 μM | 3.75 μM |
|---|---|---|---|
| PC/PS |  |  |  |
| 100/0 | 100% | 86% | 75% |
| 75/25 | 100% | 100% | 89% |
| 70/30 | 100% | 100% | 100% |
| pH |  |  |  |
| 7.5 | 100% | 86% | 75% |
| 6 | 100% | 100% | 95% |
| 5 | 100% | 100% | 100% |
| 4 | 100% | 100% | 100% |
| Osmotic pressure between leaflets of vesicles |  |  |  |
| 150 mM NaCl | 100% | 86% | 75% |
| 300 mM NaCl | 100% | 100% | 89% |
| 450 mM NaCl | 100% | 100% | 91% |
| 600 mM NaCl | 100% | 100% | 95% |

As indicated above, when lower concentrations of AH peptide were used, varying conditions of temperature, lipid composition of vesicles, pH or osmotic pressure between leaflets of vesicles significantly altered the efficiency of the AH peptide mediated lysis of vesicles. For example, by increasing the temperature from 25 deg. C. to 30 deg. C. while using AH peptide at a concentration of 3.75 μM, vesicle lysis was increased from 75% to 100%. A similar effect was seen when the pH was decreased from 7.5 to 5 or 4 while using 3.75 μM AH peptide. In addition, by increasing osmotic pressure between leaflets of vesicles through an increase in NaCl concentration from 150 mM to 600 mM, while using AH peptide at a concentration of 3.75 μM, vesicle lysis was increased from 75% to 95%.

Example 6

Infectivity Assays Demonstrating AH Peptide-Mediated Disruption of Virus Particles for Small (HCV) but not Large (Vaccinia)

Lipid vesicles represent a widely-used model for enveloped viruses. In order to demonstrate that AH peptides have a similar disruptive effect on the lipid envelopes of viruses, inoculums of HCV (avg. particle diameter of 50 nm) and Vaccinia virus (avg. particle diameter of 360 nm), were treated with either AH or control NH peptides according to the following protocol.

Infectious viral stocks of HCV and Vaccinia virus were prepared as described previously (Elazer et al. (2003) *Virol.* 77:6055-61; and Sklan et al. (2007) *J. Virol.* 81:11096-105). Peptides were reconstituted in water at a concentration of 0.26 mM and stored at −80° C. Peptides were diluted in serum free medium containing 300 focus-forming units (FFU) of HCV or 50 plaque forming units (PFU) of Vaccinia virus to a final concentration of 13 μM and incubated at room temperature for 0.5 h. The virus-peptide mixtures were then used to infect Huh 7.5 cells in a 96-well plate for HCV or CV1 cells in 6 well plates for Vaccinia virus. After adsorption for 2 h at 37° C., the inocula were removed and fresh growth medium was added to the cells for 3 days. Huh 7.5 cells were then fixed with 4% formaldehyde and immunostained with primary antibody against HCV structural protein core (Matto et al. (2004) *J. Virol* 78:12047-53), and secondary antibody conjugated to Alexa 594™. The number of HCV-positive foci was counted by fluorescence microscopy. Vaccinia virus plaques were counted following cell fixation and staining with crystal violet. Results are expressed as a percentage of the infectivity associated with the non-peptide treated control inoculum.

Figure 11:
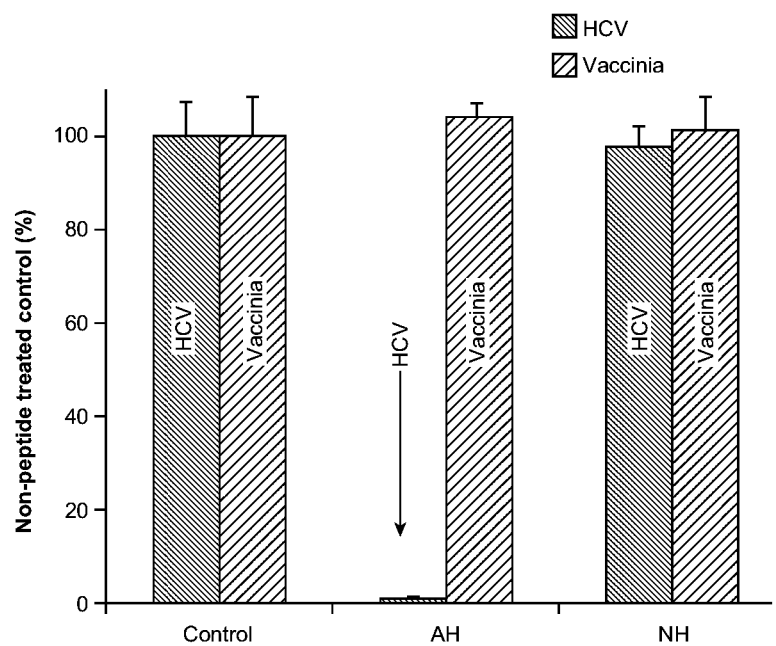
FIG. 11 provides a graph which shows the results of infectivity assays for HCV and Vaccinia virus inoculums treated with AH or NH peptide.

As shown in FIG. 11, AH, but not NH, peptide treatment dramatically reduced the infectivity of HCV particles (avg. particle diameter of 50 nm). By contrast, analogous experiments performed with vaccinia virus (avg. particle diameter of 360 nm) exhibited little AH peptide-induced disruption of infectious virus particles (see FIG. 11).

These results demonstrate that when present in an isolated, non-natural context, the AH peptide is a potent mediator of lipid vesicle and lipid membrane-bound virus particle lysis. The efficiency of this activity exhibits a size dependence that falls within the range of a wide array of medically-important viruses.

Example 7

Further Characterization of Size-Dependent AH Peptide-Mediated Lysis

Additional experiments were conducted as described below in order to further characterize the size-dependent AH peptide-mediated lysis of vesicles. In order to capture the vesicle lysis potency of the AH peptide, we constructed a biomimetic, self-assembled intact vesicle platform on a gold-coated quartz crystal using a detection system with nano-mass range precision. This technique measures not only the quantitative binding mass, but also the viscoelasticity of the adlayer.

Materials and Methods

Quartz Crystal Microbalance-Dissipation (QCM-D)

Adsorption kinetics and the properties of the adsorbed layer were studied using a Q-Sense E-4, multiple channel system (Q-Sense AB, Gothenburg, Sweden). Note that this system is different than that used for Examples 1-4 above. The samples are introduced using a peristaltic pump with flow rate of 0.1 ml/min. AT-cut gold crystals (Q-Sense) of 14 mm in diameter with 50 nm thermally evaporated gold were used for the vesicle interaction and adsorption experiments described below. Each QCM crystal was treated with oxygen plasma at ~80 watts for ~3 minutes prior to measurements (March Plasmod Plasma Etcher, March Instruments, California, USA). The crystal was initially driven near its resonance frequency as indicated by a maximum in the current. To capture the characteristic dissipation, the drive circuit was short-circuited and the exponential decay of the crystal oscillation was recorded and analyzed, yielding the frequency and dissipation changes at 5, 15, 25, 35, 45, 55 and 65 MHz. The temperature of the Q-Sense cell was set at 25.0° C. and accurately controlled by a Peltier element in the cell with fluctuation smaller than ±0.05° C. All experiments were repeated at least three times, with a standard deviation of less than 1%.

Small Unilamellar Vesicle Preparation

Vesicles of 1-palmitoyl-2-oleoyl-sn-glycero-3-phosphocholine (POPC) (Avanti Polar Lipids, Alabaster, USA) with different size distributions were prepared by the combination of freeze-thaw cycles and extrusion method. Throughout the experiments, we used a Tris buffer (10 mM Tris, pH 7.5 and 150 mM NaCl) in 18.2 MΩ-cm MilliQ water (MilliPore, Oregon, USA). Extruded vesicles (referred to simply as vesicles) were prepared in the following manner. Lipid films were prepared by first drying the as-supplied lipids dissolved in chloroform under a gentle stream of nitrogen at room temperature. Then the resulting lipid film was stored under vacuum for at least 5 hours in order to remove residual chloroform. Vesicles were prepared by first swelling the lipid film in aqueous solution then vortexing periodically for 5 min. The resulting vesicle solutions were subsequently sized by a mini extruder (Avanti Polar Lipids, Alabaster, USA) through polycarbonate membranes with nominal sizes of 1000-nm, 400-nm, 200-nm, 100-nm, 50-nm and 30-nm pores. Vesicles were generally prepared at a nominal lipid concentration of ~5 mg/ml then subsequently diluted before experiments. Vesicles were generally used within a day of preparation.

Peptides

Amphipathic α-helical peptides (AH) and non-amphipathic non-helical peptides (NH) were synthesized by Anaspec Corporation (San Jose, Calif., USA). Whereas the AH peptide is helical with an extended hydrophobic domain, NH peptides were designed to introduce three charged amino acids (underlined). The sequences of AH and NH peptide are H-Ser-Gly-Ser-Trp-Leu-Arg-Asp-Val-Trp-Asp-Trp-Ile-Cys-Thr-Val-Leu-Thr-Asp-Phe-Lys-Thr-Trp-Leu-Gln-Ser-Lys-Leu-NH2 (SEQ ID NO: 32) and H-Ser-Gly-Ser-Trp-Leu-Arg-Asp-Asp-Trp-Asp-Trp-Glu-Cys-Thr-Val-Leu-Thr-Asp-Asp-Lys-Thr-Trp-Leu-Gln-Ser-Lys-Leu-NH2 (SEQ ID NO: 91), respectively.

Results

Figure 12:
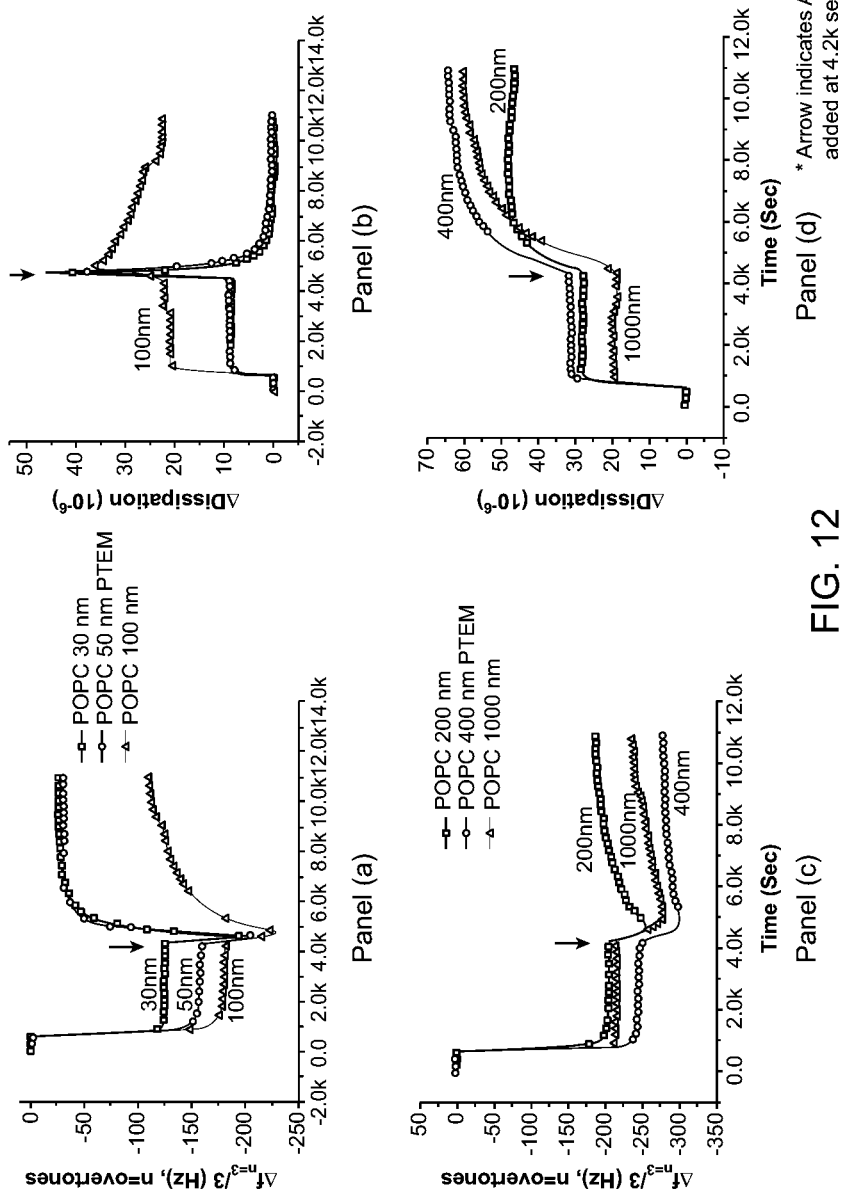
FIG. 12 shows the frequency response for various vesicle size distributions up to 100 nm upon AH peptide addition (A), corresponding energy dissipation changes (B), QCM frequency response for vesicle size distribution "Non-native", "non-endogenous", and "heterologous", in the context of a polypeptide, are used interchangeably herein to refer to a polypeptide having an amino acid sequence or, in the context of an expression system or a viral particle, present in an environment different to that found in nature.

Two distinct binding kinetics and viscoelastic behaviors were identified, as a function of deposited vesicle size: a) the formation of a rigid bilayer by vesicle rupture via interaction with AH peptide (FIG. 12, Panels A and B), and b) AH peptide binding on intact vesicles that remain as a stable layer (FIG. 12, Panels C and D).

Figure 13:
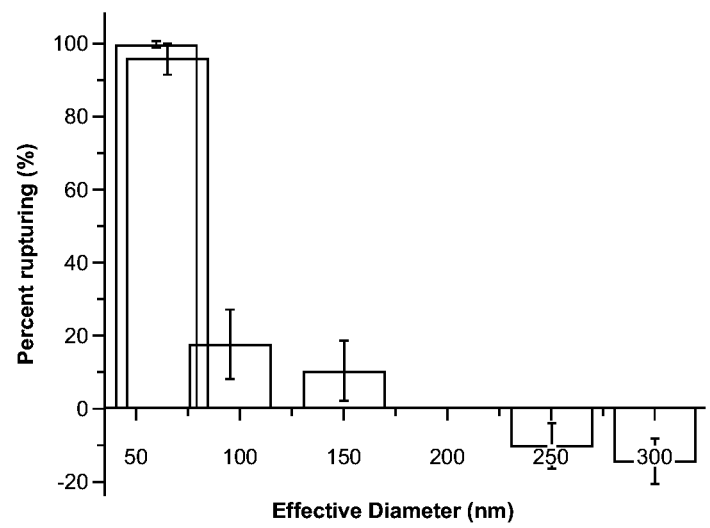

In addition two distinct potencies of the AH peptide were identified: a) a complete rupture and bilayer formation for vesicles with an average size range from 54 nm to 72 nm, and b) for vesicles with an average size distribution greater than 90 nm a reduced potency, such that the AH peptides do not completely rupture vesicles. Without intending to be bound by any particular theory, it is presumed that this is a result of the significant difference in the radii of the vesicle curvatures of average size distribution of 55 nm versus 95 nm. The lack of formation of a complete bilayer from the larger vesicles is evidenced by rupturing percent decrease from 99% to 12% (FIG. 13). This is demonstrated by a decrease of the final frequency by 125±12 Hz (compared to 25 Hz for a complete bilayer) and a maximum decrease of the dissipation shift to only $23 \times 10^{-6}$ (compared to $0.08 \times 10^{-6}$ for a complete bilayer) as shown in FIG. 12. Moreover, the ability of the AH peptide to induce the lysis of vesicles further lessened when the average vesicle size distribution became greater than 150 nm, as shown by the AH peptide binding on vesicle assemblies with resulting increase in total bound mass (FIG. 12, Panels C and D; and FIG. 13). The negative values for percent rupturing of vesicles having an effective diameter of about 250 nm to about 300 nm are a result of the frequency values measured upon binding of the AH peptide on vesicle assemblies.

Example 8

Viscoelastic Modeling for Two Different Regions of a Biomimetic Intact Vesicle Platform Induced by Interactions with AH Peptides Derived from Hepatitis C Virus In order to gain insight into the structural changes of the biomimetic platform on the solid support shown in FIG. 12. The Voigt-Voinova model was employed to evaluate the experimentally measured $\Delta f$ and $\Delta D$ for two different platforms (intact vesicle radius ~60 nm and intact vesicle radius ~300 nm). Briefly, the Voigt-Voinova model treats a biomimetic platform as a single Voigt element and the quartz crystal is assumed to be purely elastic, and the surrounding solution is assumed to be purely viscous and Newtonian. Further, the thickness and density of the platform are assumed to be uniform with no slip between the platform and the crystal during shearing. Since the platform is represented with a homogeneous film on the crystal using four unknown parameters (ρP, tP, μP, ηP) and above the platform is a semi-infinite bulk liquid (ρ1, η1), overtones were fitted to this model using the commercial program, Q-tools software (Q-Sense AB).

QCM-D E4 has multiple channels that allows for concurrent measurements of Δf and ΔD at the first, third, etc., overtone (n=1, 3, . . . ; i.e., f=5 MHz, 15 MHz, . . . ) up to n=13 to obtain the resonant frequencies, fn=1, fn=3, etc., and the corresponding dissipation values, Dn=1, Dn=3, etc., with a repetition rate of ~1 Hz. Since the linear relationship between the adsorbed mass and the change in frequency (Sauerbrey model) is not necessarily valid for viscoelastic films, which exhibit additional energy dissipations as well as frequency-(overtone) dependent responses, this type of information is very important in understanding complex biomembrane research.

The adsorption kinetics of intact vesicles with different radii were followed and then AH peptides were added. This allowed for analysis of the characteristic kinetics of the intact vesicle transformation to a complete bilayer on a pure gold solid substrate resulting from the addition of an AH peptide. The simultaneous measurements of changes in frequency, Δfn, and energy dissipation, ΔDn, obtained at four different overtones (n=1 for the fundamental and 3, 5, 7, 9, 11, and 13 for the overtones) were determined as a function of time. By employing the Voigt model, it is possible to obtain measurements of two or more harmonics. The Sauerbrey and Voigt models were employed to calculate the thickness for the entire range of kinetic measurements demonstrating that for a "rigid" bilayer of ~5 nm, the Sauerbrey model severely underestimates the thickness of the viscoelastic intact vesicle platform (~22 nm), as opposed to the more accurate Voigt model (~45 nm). The characteristic shear modulus (μP) and viscosity (ηP) increased as thickness decreased. In other words, these two physical parameters confirmed that the platform had been changed from soft intact vesicles to a bilayer.

In marked contrast, when biomimetic, self-assembled intact vesicles with diameter ~300 nm were created, no viscoelastic changes were observed in the platform due to interactions with the AH peptide. The stability of the frequency and dissipation of the bare gold crystal over 600 seconds was verified. Upon the addition of a vesicle solution (0.1 mg/ml), a rapid mass uptake was observed followed by a decrease in QCM-D frequency, reaching saturation. Note that the Sauerbrey model predicts that these normalized frequency changes should be independent of overtone, which is not observed experimentally. This adsorption process is accompanied by an increase in ΔD, reaching saturation. The vesicles were saturated for 3000 seconds, and subsequently, the AH peptide was introduced. An initial binding and a large subsequent increase in $\Delta f_n$ and decrease in $\Delta D_n$ was detected. In contrast to the vesicle to bilayer transformation case, AH bound to the intact vesicle platform and stabilized within 600 sec. This view was also confirmed by the Sauerbrey and Voigt thickness calculations. As AH peptides bind on the intact vesicle platform, due to high energy dissipation change, the Voigt thickness dramatically increases, more so than does the Sauerbrey thickness. In addition, the characteristic shear modulus ($\mu_P$) and viscosity ($\eta_P$) either does not change or slightly decreases, as compared with the vesicle-bilayer transformation platform case.

These results show two distinct kinetics depending on the radii of the intact vesicles: a) for intact vesicles less than ~60 nm, the AH peptide promotes rupturing to form a bilayer; b) for intact vesicles larger than ~300 nm, the AH peptide does not promote rupturing, but rather binds on the intact vesicle platform. The platform can therefore be used as an effective means of detecting interactions with AH peptides.

What is claimed is:

1. A method of inactivating an enveloped virus, the method comprising:

contacting an enveloped virus having an average particle diameter of less than 150 nm with an amphipathic α-helical (AH) peptide in an amount and under conditions effective to facilitate disruption of the viral envelope, with the proviso that the enveloped virus is other than hepatitis C virus (HCV), wherein the AH peptide is from the N-terminal alpha-helix of hepatitis C virus (HCV) nonstructural protein NS5A, wherein said contacting is effective to disrupt the viral envelope of the virus, thereby reducing infectivity of the virus.

2. The method of claim 1, wherein the enveloped virus is present in a biological fluid.

3. The method of claim 2, wherein the biological fluid is blood.

4. The method of claim 3, wherein the biological fluid is extracorporeal.

5. The method of claim 1, wherein said conditions include a pH of 7.5 or less.

6. The method of claim 5, wherein said conditions include a pH of 7.0 or less.

7. The method of claim 6, wherein said conditions include a pH of 6.5 or less.

8. The method of claim 7, wherein said conditions include a pH of 6.0 or less.

9. The method of claim 8, wherein said conditions include a pH of 5.5 or less.

10. The method of claim 9, wherein said conditions include a pH of 5.0 or less.

11. The method of claim 10, wherein said conditions include a pH of 4.5 or less.

12. The method of claim 11, wherein said conditions include a pH of 4.0 or less.

13. The method of claim 1, wherein said conditions include a temperature of 20° C. or greater.

14. The method of claim 13, wherein said conditions include a temperature of 25° C. or greater.

15. The method of claim 14, wherein said condition include a temperature of 30° C. or greater.

16. A method for treating in vitro or ex vivo biological fluid, comprising:

contacting an isolated biological fluid with an effective amount of an amphipathic α-helical (AH) peptide from the N-terminal alpha-helix of hepatitis C virus (HCV) nonstructural protein NS5A;

wherein said contacting provides for disruption of an enveloped virus that may be present in the biological fluid, wherein the enveloped virus has an average particle diameter of less than 150 nm and is other than hepatitis C virus.

17. The method of claim 16, wherein said contacting is accomplished by mixing the biological fluid with a composition comprising the AH peptide.

18. The method of claim 16, wherein the AH peptide is immobilized on a surface of a substrate.

19. A method for decreasing a level of an enveloped virus contaminating a material, the method comprising:

treating a material with an effective amount of an amphipathic α-helical (AH) peptide, wherein said treating is effective to disrupt at least 25% of enveloped viral particles that may be associated with the material, wherein the enveloped virus has an average particle diameter of less than 150 nm and is other than hepatitis C virus, wherein the AH peptide is from the N-terminal alpha-helix of hepatitis C virus (HCV) nonstructural protein NS5A.

20. The method of claim 19, wherein the material is a biological fluid.

21. The method of claim 20, wherein the biological fluid is in a container.

22. The method of claim 20, wherein the biological fluid is blood or a blood product.

23. The method of claim 19, wherein the material is a biological tissue.

24. The method of claim 23, wherein the biological tissue is an organ for transplant.

25. The method of claim 22, wherein the blood product is plasma.

26. The method of claim 19, further comprising removing all or a portion of the AH peptide and/or disrupted enveloped viral particle from the material after treating.

27. The method of claim 1, wherein the AH peptide comprises an amino acid sequence of the formula:

$SWLX_1X_2X_3X_4X_5WX_6X_7X_8X_9X_{10}$ (SEQ ID NO:1), wherein $X_1$ is a charged residue or a polar residue; $X_2$ is any amino acid residue; $X_3$ is other than a charged residue; $X_4$ is a nonpolar residue; $X_5$ is a charged residue or a polar, uncharged residue; $X_6$ is other than a charged residue; $X_7$ is a polar, uncharged residue, a nonpolar residue, or a negatively charged residue; $X_8$ is a polar, uncharged residue, a nonpolar residue, or a positively charged residue; $X_9$ is a nonpolar residue; and $X_{10}$ is C or L.

28. The method of claim 1, wherein the AH peptide comprises an amino acid sequence as set forth in any one of SEQ ID NOs:2-77.

29. The method of claim 1, wherein the AH peptide has a length of from 14 amino acids to 30 amino acids.

* * * * *

UNITED STATES PATENT AND TRADEMARK OFFICE
CERTIFICATE OF CORRECTION

PATENT NO. : 8,728,793 B2
APPLICATION NO. : 12/172796
DATED : May 20, 2014
INVENTOR(S) : Jeffrey Glenn et al.

It is certified that error appears in the above-identified patent and that said Letters Patent is hereby corrected as shown below:

In the specification

Column 1, lines 7-10

Under FEDERALLY-SPONSORED RESEARCH OR DEVELOPMENT:

"This invention was made with Government support under contracts NAG8-1843 awarded by the NASA aid DK064223 awarded by the National Institutes of Health. The Government has certain rights in this invention."

should be replaced with:

-- This invention was made with Government support under contract NAG8-1843 awarded by NASA and under contract DK064223 awarded by the National Institutes of Health. The Government has certain rights in the invention. --

Signed and Sealed this
Twenty-second Day of March, 2016

Michelle K. Lee
*Director of the United States Patent and Trademark Office*